United States Patent
Bardy

(10) Patent No.: US 10,736,529 B2
(45) Date of Patent: Aug. 11, 2020

(54) SUBCUTANEOUS INSERTABLE ELECTROCARDIOGRAPHY MONITOR

(71) Applicant: Bardy Diagnostics, Inc., Seattle, WA (US)

(72) Inventor: Gust H. Bardy, Carnation, WA (US)

(73) Assignee: BARDY DIAGNOSTICS, INC., Seattle, WA (US)

( * ) Notice: Subject to any disclaimer, the term of this patent is extended or adjusted under 35 U.S.C. 154(b) by 0 days.

(21) Appl. No.: 16/178,444

(22) Filed: Nov. 1, 2018

(65) Prior Publication Data
US 2019/0069798 A1    Mar. 7, 2019

Related U.S. Application Data

(63) Continuation-in-part of application No. 15/905,715, filed on Feb. 26, 2018, and a continuation-in-part of (Continued)

(51) Int. Cl.
*A61B 5/00* (2006.01)
*A61B 5/0408* (2006.01)
(Continued)

(52) U.S. Cl.
CPC ........ *A61B 5/04085* (2013.01); *A61B 5/0022* (2013.01); *A61B 5/04017* (2013.01);
(Continued)

(58) Field of Classification Search
CPC . A61B 5/04085; A61B 5/0452; A61B 5/4809; A61B 5/1118; A61B 5/1117;
(Continued)

(56) References Cited

U.S. PATENT DOCUMENTS 3,215,136 A    11/1965    Holter et al.
3,569,852 A    3/1971     Berkovits
(Continued)

FOREIGN PATENT DOCUMENTS

DE    19955211    5/2001
EP    1859833     11/2007
(Continued)

OTHER PUBLICATIONS 15 of the Hottest Wearable Gadgets, URL <http://thehottestgadgets.com/2008/09/the-15-hottest-wearable-gadgets-001253> (Web page cached on Sep. 27, 2008).
(Continued)

*Primary Examiner* — Scott M. Getzow
(74) *Attorney, Agent, or Firm* — Patrick J. S. Inouye; Leonid Kisselev

(57) ABSTRACT

Long-term electrocardiographic and physiological monitoring over a period lasting up to several years in duration can be provided through a continuously-recording subcutaneous insertable cardiac monitor (ICM). The sensing circuitry and the physical layout of the electrodes are specifically optimized to capture electrical signals from the propagation of low amplitude, relatively low frequency content cardiac action potentials, particularly the P-waves that are generated during atrial activation. The ICM is intended to be implanted centrally and positioned axially and slightly to either the left or right of the sternal midline in the parasternal region of the chest, with at least one of the ECG sensing electrodes of the ICM being disposed for being positioned in a region overlying the sternum or adjacent to the sternum and the other of the electrodes also being disposed for being positioned over the sternum or adjacent to the sternum of on the patient's chest.

16 Claims, 8 Drawing Sheets

Related U.S. Application Data application No. 15/832,385, filed on Dec. 5, 2017, and a continuation of application No. 15/406,627, filed on Jan. 13, 2017, now Pat. No. 9,901,274, which is a continuation of application No. 14/080,717, filed on Nov. 14, 2013, now Pat. No. 9,545,204.

(60) Provisional application No. 61/882,403, filed on Sep. 25, 2013.

(51) Int. Cl.

| | | |
|---|---|---|
| *A61B 5/04* | (2006.01) | |
| *A61B 5/0432* | (2006.01) | |
| *A61B 5/11* | (2006.01) | |
| *A61B 5/0452* | (2006.01) | |
| *A61B 5/0428* | (2006.01) | |
| *A61B 5/042* | (2006.01) | |
| *A61B 5/145* | (2006.01) | |
| *A61B 5/08* | (2006.01) | |
| *A61B 5/0205* | (2006.01) | |
| *A61B 5/021* | (2006.01) | |
| *A61B 5/087* | (2006.01) | |
| *A61B 5/1455* | (2006.01) | |
| *G01N 27/30* | (2006.01) | |
| *A61B 5/01* | (2006.01) | |
| *A61B 5/091* | (2006.01) | |

(52) U.S. Cl.
CPC .......... *A61B 5/0422* (2013.01); *A61B 5/0452* (2013.01); *A61B 5/04087* (2013.01); *A61B 5/04286* (2013.01); *A61B 5/04325* (2013.01); *A61B 5/04525* (2013.01); *A61B 5/1116* (2013.01); *A61B 5/1117* (2013.01); *A61B 5/1118* (2013.01); *A61B 5/4809* (2013.01); *A61B 5/6801* (2013.01); *A61B 5/686* (2013.01); *A61B 5/6823* (2013.01); *A61B 5/6833* (2013.01); *A61B 5/6867* (2013.01); *A61B 5/0006* (2013.01); *A61B 5/01* (2013.01); *A61B 5/021* (2013.01); *A61B 5/02055* (2013.01); *A61B 5/087* (2013.01); *A61B 5/0816* (2013.01); *A61B 5/091* (2013.01); *A61B 5/14532* (2013.01); *A61B 5/14542* (2013.01); *A61B 5/14551* (2013.01); *A61B 5/7455* (2013.01); *A61B 2505/07* (2013.01); *A61B 2560/0271* (2013.01); *A61B 2560/045* (2013.01); *A61B 2560/0412* (2013.01); *A61B 2560/0468* (2013.01); *A61B 2562/0219* (2013.01); *A61B 2562/164* (2013.01); *G01N 27/307* (2013.01)

(58) Field of Classification Search
CPC .............. A61B 5/6823; A61B 5/04525; A61B 5/04087; A61B 5/0022; A61B 5/0006; A61B 5/02055; A61B 5/1116; A61B 5/04017; A61B 5/04325; A61B 5/6833; A61B 5/6801; A61B 2560/0412
See application file for complete search history.

(56) References Cited

U.S. PATENT DOCUMENTS

| | | |
|---|---|---|
| 3,602,215 A | 8/1971 | Parnell |
| 3,699,948 A | 10/1972 | Ota et al. |
| 3,718,772 A | 2/1973 | Sanctuary |
| 3,893,453 A | 7/1975 | Goldberg |
| 4,123,785 A | 10/1978 | Cherry et al. |
| 4,151,513 A | 4/1979 | Menken et al. |
| 4,328,814 A | 5/1982 | Arkans |
| 4,441,500 A | 4/1984 | Sessions et al. |
| 4,532,934 A | 8/1985 | Kelen |
| 4,546,342 A | 10/1985 | Weaver et al. |
| 4,550,502 A | 11/1985 | Grayzel |
| 4,580,572 A | 4/1986 | Granek et al. |
| 4,635,646 A | 1/1987 | Gilles et al. |
| 4,653,022 A | 3/1987 | Koro |
| 4,716,903 A | 1/1988 | Hansen |
| 4,809,705 A | 3/1989 | Ascher |
| 4,915,656 A | 4/1990 | Alferness |
| 5,007,429 A | 4/1991 | Treatch et al. |
| 5,025,794 A | 6/1991 | Albert et al. |
| 5,107,480 A | 4/1992 | Naus |
| 5,168,876 A | 12/1992 | Quedens et al. |
| 5,215,098 A | 6/1993 | Steinhaus |
| 5,231,990 A | 8/1993 | Gauglitz |
| D341,423 S | 11/1993 | Bible |
| 5,263,481 A | 11/1993 | Axelgaard |
| 5,265,579 A | 11/1993 | Ferrari |
| 5,333,615 A | 8/1994 | Craelius et al. |
| 5,341,806 A | 8/1994 | Gadsby et al. |
| 5,348,008 A * | 9/1994 | Bornn .................. A61B 5/0006 600/301 |
| 5,355,891 A | 10/1994 | Wateridge et al. |
| 5,365,934 A | 11/1994 | Leon et al. |
| 5,365,935 A | 11/1994 | Righter et al. |
| 5,392,784 A | 2/1995 | Gudaitis |
| D357,069 S | 4/1995 | Plahn et al. |
| 5,402,780 A | 4/1995 | Faasse, Jr. |
| 5,402,884 A | 4/1995 | Gilman et al. |
| 5,450,845 A | 9/1995 | Axelgaard |
| 5,451,876 A | 9/1995 | Sendford et al. |
| 5,458,141 A | 10/1995 | Neil |
| 5,473,537 A | 12/1995 | Glazer et al. |
| 5,483,969 A | 1/1996 | Testerman et al. |
| 5,511,553 A | 4/1996 | Segalowitz |
| 5,540,733 A | 7/1996 | Testerman et al. |
| 5,546,952 A | 8/1996 | Erickson |
| 5,549,655 A | 8/1996 | Erickson |
| 5,579,919 A | 12/1996 | Gilman et al. |
| 5,582,181 A | 12/1996 | Ruess |
| D377,983 S | 2/1997 | Sabri et al. |
| 5,601,089 A | 2/1997 | Bledsoe et al. |
| 5,623,935 A | 4/1997 | Faisandier |
| 5,682,901 A | 11/1997 | Kamen |
| 5,697,955 A | 12/1997 | Stolte |
| 5,724,967 A | 3/1998 | Venkatachalam |
| 5,749,902 A | 5/1998 | Olsen et al. |
| 5,788,633 A | 8/1998 | Mahoney |
| 5,817,151 A | 10/1998 | Olsen et al. |
| 5,819,741 A | 10/1998 | Karlsson et al. |
| 5,850,920 A | 12/1998 | Gilman et al. |
| D407,159 S | 3/1999 | Roberg |
| 5,876,351 A | 3/1999 | Rohde |
| 5,906,583 A | 5/1999 | Rogel |
| 5,951,598 A | 9/1999 | Bishay et al. |
| 5,957,857 A | 9/1999 | Hartley |
| 5,984,102 A | 11/1999 | Tay |
| 6,032,064 A | 2/2000 | Devlin et al. |
| 6,038,469 A | 3/2000 | Karlsson et al. |
| 6,101,413 A | 8/2000 | Olsen et al. |
| 6,115,638 A | 9/2000 | Groenke |
| 6,117,077 A | 9/2000 | Del Mar et al. |
| 6,134,479 A | 10/2000 | Brewer et al. |
| 6,148,233 A | 11/2000 | Owen et al. |
| 6,149,602 A | 11/2000 | Arcelus |
| 6,149,781 A | 11/2000 | Forand |
| 6,188,407 B1 | 2/2001 | Smith et al. |
| D443,063 S | 5/2001 | Pisani et al. |
| 6,245,025 B1 | 6/2001 | Torok et al. |
| 6,246,330 B1 | 6/2001 | Nielsen |
| 6,249,696 B1 | 6/2001 | Olson et al. |
| D445,507 S | 7/2001 | Pisani et al. |
| 6,269,267 B1 | 7/2001 | Bardy et al. |
| 6,272,385 B1 | 8/2001 | Bishay et al. |
| 6,298,255 B1 | 10/2001 | Cordero et al. |
| 6,301,502 B1 | 10/2001 | Owen et al. |
| 6,304,773 B1 | 10/2001 | Taylor et al. |
| 6,304,780 B1 | 10/2001 | Owen et al. |

(56) References Cited

U.S. PATENT DOCUMENTS

| | | |
|---|---|---|
| 6,304,783 B1 | 10/2001 | Lyster et al. |
| 6,374,138 B1 | 4/2002 | Owen et al. |
| 6,381,482 B1 | 4/2002 | Jayaraman et al. |
| 6,416,471 B1 | 7/2002 | Kumar et al. |
| 6,418,342 B1 | 7/2002 | Owen et al. |
| 6,424,860 B1 | 7/2002 | Karlsson et al. |
| 6,427,083 B1 | 7/2002 | Owen et al. |
| 6,427,085 B1 | 7/2002 | Boon et al. |
| 6,454,708 B1 | 9/2002 | Ferguson et al. |
| 6,456,872 B1 | 9/2002 | Faisandier |
| 6,463,320 B1 | 10/2002 | Xue et al. |
| 6,546,285 B1 | 4/2003 | Owen et al. |
| 6,605,046 B1 | 8/2003 | Del Mar |
| 6,607,485 B2 | 8/2003 | Bardy |
| 6,611,705 B2 | 8/2003 | Hopman et al. |
| 6,671,545 B2 | 12/2003 | Fincke |
| 6,671,547 B2 | 12/2003 | Lyster et al. |
| 6,694,186 B2 | 2/2004 | Bardy |
| 6,704,595 B2 | 3/2004 | Bardy |
| 6,705,991 B2 | 3/2004 | Bardy |
| 6,719,701 B2 | 4/2004 | Lade |
| 6,754,523 B2 | 6/2004 | Toole |
| 6,782,293 B2 | 8/2004 | Dupelle et al. |
| 6,856,832 B1 | 2/2005 | Matsumura |
| 6,860,897 B2 | 3/2005 | Bardy |
| 6,866,629 B2 | 3/2005 | Bardy |
| 6,887,201 B2 | 5/2005 | Bardy |
| 6,893,397 B2 | 5/2005 | Bardy |
| 6,895,261 B1 | 5/2005 | Palamides |
| 6,904,312 B2 | 6/2005 | Bardy |
| 6,908,431 B2 | 6/2005 | Bardy |
| 6,913,577 B2 | 7/2005 | Bardy |
| 6,944,498 B2 | 9/2005 | Owen et al. |
| 6,960,167 B2 | 11/2005 | Bardy |
| 6,970,731 B1 | 11/2005 | Jayaraman et al. |
| 6,978,169 B1 | 12/2005 | Guerra |
| 6,993,377 B2 | 1/2006 | Flick et al. |
| 7,020,508 B2 | 3/2006 | Stivoric et al. |
| 7,027,864 B2 | 4/2006 | Snyder et al. |
| 7,065,401 B2 | 6/2006 | Worden |
| 7,085,601 B1 | 8/2006 | Bardy et al. |
| 7,104,955 B2 | 9/2006 | Bardy |
| 7,134,996 B2 | 11/2006 | Bardy |
| 7,137,389 B2 | 11/2006 | Berthon-Jones |
| 7,147,600 B2 | 12/2006 | Bardy |
| 7,215,991 B2 | 5/2007 | Besson et al. |
| 7,248,916 B2 | 7/2007 | Bardy |
| 7,257,438 B2 | 8/2007 | Kinast |
| 7,277,752 B2 | 10/2007 | Matos |
| 7,294,108 B1 | 11/2007 | Bornzin et al. |
| D558,882 S | 1/2008 | Brady |
| 7,328,061 B2 | 2/2008 | Rowlandson et al. |
| 7,412,395 B2 | 8/2008 | Rowlandson et al. |
| 7,429,938 B1 | 9/2008 | Corndorf |
| 7,552,031 B2 | 6/2009 | Vock et al. |
| D606,656 S | 12/2009 | Kobayashi et al. |
| 7,706,870 B2 | 4/2010 | Shieh et al. |
| 7,756,721 B1 | 7/2010 | Falchuk et al. |
| 7,787,943 B2 | 8/2010 | McDonough |
| 7,874,993 B2 | 1/2011 | Bardy |
| 7,881,785 B2 | 2/2011 | Nassif et al. |
| D639,437 S | 6/2011 | Bishay et al. |
| 7,959,574 B2 | 6/2011 | Bardy |
| 8,108,035 B1 | 1/2012 | Bharmi |
| 8,116,841 B2 | 2/2012 | Bly et al. |
| 8,135,459 B2 | 3/2012 | Bardy et al. |
| 8,172,761 B1 | 5/2012 | Rulkov et al. |
| 8,180,425 B2 | 5/2012 | Selvitelli et al. |
| 8,200,320 B2 | 6/2012 | Kovacs |
| 8,231,539 B2 | 7/2012 | Bardy |
| 8,231,540 B2 | 7/2012 | Bardy |
| 8,239,012 B2 | 8/2012 | Felix et al. |
| 8,249,686 B2 | 8/2012 | Libbus et al. |
| 8,260,414 B2 | 9/2012 | Nassif et al. |
| 8,266,008 B1 | 9/2012 | Siegal et al. |
| 8,277,378 B2 | 10/2012 | Bardy |
| 8,285,356 B2 | 10/2012 | Bly et al. |
| 8,285,370 B2 | 10/2012 | Felix et al. |
| 8,308,650 B2 | 11/2012 | Bardy |
| 8,366,629 B2 | 2/2013 | Bardy |
| 8,374,688 B2 | 2/2013 | Libbus et al. |
| 8,412,317 B2 | 4/2013 | Mazar |
| 8,460,189 B2 | 6/2013 | Libbus et al. |
| 8,473,047 B2 | 6/2013 | Chakravarthy et al. |
| 8,478,418 B2 | 7/2013 | Fahey |
| 8,538,503 B2 | 9/2013 | Kumar et al. |
| 8,554,311 B2 | 10/2013 | Warner et al. |
| 8,560,046 B2 | 10/2013 | Kumar et al. |
| 8,591,430 B2 | 11/2013 | Amurthur et al. |
| 8,594,763 B1 | 11/2013 | Bibian et al. |
| 8,600,486 B2 | 12/2013 | Kaib et al. |
| 8,613,708 B2 | 12/2013 | Bishay et al. |
| 8,613,709 B2 | 12/2013 | Bishay et al. |
| 8,620,418 B1 | 12/2013 | Kuppuraj et al. |
| 8,626,277 B2 | 1/2014 | Felix et al. |
| 8,628,020 B2 | 1/2014 | Beck |
| 8,668,653 B2 | 3/2014 | Nagata et al. |
| 8,684,925 B2 | 4/2014 | Manicka et al. |
| 8,688,190 B2 | 4/2014 | Libbus et al. |
| 8,718,752 B2 | 5/2014 | Libbus et al. |
| 8,744,561 B2 | 6/2014 | Fahey |
| 8,774,932 B2 | 7/2014 | Fahey |
| 8,790,257 B2 | 7/2014 | Libbus et al. |
| 8,790,259 B2 | 7/2014 | Katra et al. |
| 8,795,174 B2 | 8/2014 | Manicka et al. |
| 8,798,729 B2 | 8/2014 | Kaib et al. |
| 8,798,734 B2 | 8/2014 | Kuppuraj et al. |
| 8,818,478 B2 | 8/2014 | Scheffler et al. |
| 8,818,481 B2 | 8/2014 | Bly et al. |
| 8,823,490 B2 | 9/2014 | Libbus et al. |
| 8,938,287 B2 | 1/2015 | Felix et al. |
| 8,965,492 B2 | 2/2015 | Baker et al. |
| 9,066,664 B2 | 6/2015 | Karjalainen |
| 9,155,484 B2 | 10/2015 | Baker et al. |
| 9,204,813 B2 | 12/2015 | Kaib et al. |
| 9,241,649 B2 | 1/2016 | Kumar et al. |
| 9,259,154 B2 | 2/2016 | Miller et al. |
| 9,277,864 B2 | 3/2016 | Yang et al. |
| 9,339,202 B2 | 5/2016 | Brockway et al. |
| 9,375,179 B2 | 6/2016 | Schultz et al. |
| 9,414,786 B1 | 8/2016 | Brockway et al. |
| 9,439,566 B2 | 9/2016 | Arne et al. |
| 9,597,004 B2 | 3/2017 | Hughes et al. |
| 9,603,542 B2 | 3/2017 | Veen et al. |
| 9,700,222 B2 | 7/2017 | Quinlan et al. |
| 9,770,182 B2 | 9/2017 | Bly et al. |
| 10,034,614 B2 | 7/2018 | Edic et al. |
| 10,045,708 B2 | 8/2018 | Dusan |
| 10,049,182 B2 | 8/2018 | Chefles et al. |
| 2002/0013538 A1 | 1/2002 | Teller |
| 2002/0013717 A1 | 1/2002 | Ando et al. |
| 2002/0016798 A1 | 2/2002 | Sakai |
| 2002/0103422 A1 | 8/2002 | Harder et al. |
| 2002/0109621 A1 | 8/2002 | Khair et al. |
| 2002/0120310 A1 | 8/2002 | Linden et al. |
| 2002/0128686 A1 | 9/2002 | Minogue et al. |
| 2002/0184055 A1 | 12/2002 | Naghavi et al. |
| 2002/0193668 A1 | 12/2002 | Munneke |
| 2003/0004547 A1 | 1/2003 | Owen et al. |
| 2003/0028811 A1 | 2/2003 | Walker et al. |
| 2003/0073916 A1 | 4/2003 | Yonce |
| 2003/0083559 A1 | 5/2003 | Thompson |
| 2003/0097078 A1 | 5/2003 | Maeda |
| 2003/0139785 A1 | 7/2003 | Riff et al. |
| 2003/0176802 A1 | 9/2003 | Galen et al. |
| 2003/0211797 A1 | 11/2003 | Hill et al. |
| 2004/0008123 A1 | 1/2004 | Carrender |
| 2004/0019288 A1 | 1/2004 | Kinast |
| 2004/0034284 A1 | 2/2004 | Aversano et al. |
| 2004/0049120 A1 | 3/2004 | Cao et al. |
| 2004/0049132 A1 | 3/2004 | Barron et al. |
| 2004/0073127 A1 | 4/2004 | Istvan et al. |
| 2004/0087836 A1 | 5/2004 | Green et al. |
| 2004/0088019 A1 | 5/2004 | Rueter et al. |

(56) References Cited

U.S. PATENT DOCUMENTS

| | | |
|---|---|---|
| 2004/0093192 A1 | 5/2004 | Hasson et al. |
| 2004/0116784 A1 | 6/2004 | Gavish |
| 2004/0148194 A1 | 7/2004 | Wellons et al. |
| 2004/0163034 A1 | 8/2004 | Colbath et al. |
| 2004/0167416 A1 | 8/2004 | Lee |
| 2004/0207530 A1 | 10/2004 | Nielsen |
| 2004/0210165 A1 | 10/2004 | Marmaropoulos et al. |
| 2004/0236202 A1 | 11/2004 | Burton |
| 2004/0243435 A1 | 12/2004 | Williams |
| 2004/0256453 A1 | 12/2004 | Lammle |
| 2004/0260188 A1 | 12/2004 | Syed et al. |
| 2004/0260192 A1 | 12/2004 | Yamamoto |
| 2005/0010139 A1 | 1/2005 | Aminian et al. |
| 2005/0096717 A1 | 5/2005 | Bishay et al. |
| 2005/0108055 A1 | 5/2005 | Ott et al. |
| 2005/0151640 A1 | 7/2005 | Hastings |
| 2005/0154267 A1 | 7/2005 | Bardy |
| 2005/0182308 A1 | 8/2005 | Bardy |
| 2005/0182309 A1 | 8/2005 | Bardy |
| 2005/0215918 A1 | 9/2005 | Frantz et al. |
| 2005/0222513 A1 | 10/2005 | Hadley et al. |
| 2005/0228243 A1 | 10/2005 | Bardy |
| 2005/0245839 A1 | 11/2005 | Stivoric et al. |
| 2005/0261564 A1 | 11/2005 | Ryu et al. |
| 2005/0275416 A1 | 12/2005 | Hervieux et al. |
| 2006/0025696 A1 | 2/2006 | Kurzweil et al. |
| 2006/0025824 A1 | 2/2006 | Freeman et al. |
| 2006/0030767 A1 | 2/2006 | Lang et al. |
| 2006/0030904 A1 | 2/2006 | Quiles |
| 2006/0041201 A1 | 2/2006 | Behbehani et al. |
| 2006/0054737 A1 | 3/2006 | Richardson |
| 2006/0084883 A1 | 4/2006 | Linker |
| 2006/0100530 A1 | 5/2006 | Kliot et al. |
| 2006/0111642 A1 | 5/2006 | Baura et al. |
| 2006/0122469 A1 | 6/2006 | Martel |
| 2006/0124193 A1 | 6/2006 | Orr et al. |
| 2006/0224072 A1 | 10/2006 | Shennib |
| 2006/0229522 A1 | 10/2006 | Barr |
| 2006/0235320 A1 | 10/2006 | Tan et al. |
| 2006/0253006 A1 | 11/2006 | Bardy |
| 2006/0264730 A1 | 11/2006 | Stivoric et al. |
| 2006/0264767 A1 | 11/2006 | Shennib |
| 2007/0003115 A1 | 1/2007 | Patton et al. |
| 2007/0038057 A1 | 2/2007 | Nam et al. |
| 2007/0050209 A1 | 3/2007 | Yered |
| 2007/0078324 A1 | 4/2007 | Wijisiriwardana |
| 2007/0078354 A1 | 4/2007 | Holland |
| 2007/0088406 A1 | 4/2007 | Bennett et al. |
| 2007/0089800 A1 | 4/2007 | Sharma |
| 2007/0093719 A1 | 4/2007 | Nichols, Jr. et al. |
| 2007/0100248 A1 | 5/2007 | Van Dam et al. |
| 2007/0100667 A1 | 5/2007 | Bardy |
| 2007/0123801 A1 | 5/2007 | Goldberger et al. |
| 2007/0131595 A1 | 6/2007 | Jansson et al. |
| 2007/0136091 A1 | 6/2007 | McTaggart |
| 2007/0179357 A1 | 8/2007 | Bardy |
| 2007/0185390 A1 | 8/2007 | Perkins et al. |
| 2007/0203415 A1 | 8/2007 | Bardy |
| 2007/0203423 A1 | 8/2007 | Bardy |
| 2007/0208232 A1 | 9/2007 | Kovacs |
| 2007/0208233 A1 | 9/2007 | Kovacs |
| 2007/0208266 A1 | 9/2007 | Hadley |
| 2007/0225611 A1 | 9/2007 | Kumar et al. |
| 2007/0244405 A1 | 10/2007 | Xue et al. |
| 2007/0249946 A1 | 10/2007 | Kumar et al. |
| 2007/0255153 A1 | 11/2007 | Kumar et al. |
| 2007/0265510 A1 | 11/2007 | Bardy |
| 2007/0276270 A1 | 11/2007 | Tran |
| 2007/0276275 A1 | 11/2007 | Proctor et al. |
| 2007/0293738 A1 | 12/2007 | Bardy |
| 2007/0293739 A1 | 12/2007 | Bardy |
| 2007/0293740 A1 | 12/2007 | Bardy |
| 2007/0293741 A1 | 12/2007 | Bardy |
| 2007/0293772 A1 | 12/2007 | Bardy |
| 2007/0299325 A1 | 12/2007 | Farrell et al. |
| 2007/0299617 A1 | 12/2007 | Willis |
| 2008/0027339 A1 | 1/2008 | Nagai et al. |
| 2008/0051668 A1 | 2/2008 | Bardy |
| 2008/0058661 A1 | 3/2008 | Bardy |
| 2008/0143080 A1 | 3/2008 | Burr |
| 2008/0088467 A1 | 4/2008 | Al-Ali et al. |
| 2008/0091089 A1 | 4/2008 | Guillory et al. |
| 2008/0091097 A1 | 4/2008 | Linti et al. |
| 2008/0108890 A1 | 5/2008 | Teng et al. |
| 2008/0114232 A1 | 5/2008 | Gazit |
| 2008/0139953 A1 | 6/2008 | Baker et al. |
| 2008/0177168 A1 | 7/2008 | Callahan et al. |
| 2008/0194927 A1 | 8/2008 | KenKnight et al. |
| 2008/0208009 A1 | 8/2008 | Shklarski |
| 2008/0208014 A1 | 8/2008 | KenKnight et al. |
| 2008/0284599 A1 | 11/2008 | Zdeblick et al. |
| 2008/0288026 A1 | 11/2008 | Cross et al. |
| 2008/0294024 A1 | 11/2008 | Cosentino et al. |
| 2008/0306359 A1 | 12/2008 | Zdeblick et al. |
| 2008/0309481 A1 | 12/2008 | Tanaka et al. |
| 2008/0312522 A1 | 12/2008 | Rowlandson et al. |
| 2009/0012412 A1 | 1/2009 | Wesel |
| 2009/0012979 A1 | 1/2009 | Bateni et al. |
| 2009/0054952 A1 | 2/2009 | Glukhovsky et al. |
| 2009/0062897 A1 | 3/2009 | Axelgaard |
| 2009/0069867 A1 | 3/2009 | KenKnight et al. |
| 2009/0073991 A1 | 3/2009 | Landrum et al. |
| 2009/0076336 A1 | 3/2009 | Mazar et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076346 A1 | 3/2009 | James et al. |
| 2009/0076349 A1 | 3/2009 | Libbus et al. |
| 2009/0076397 A1 | 3/2009 | Libbus et al. |
| 2009/0076401 A1 | 3/2009 | Mazar et al. |
| 2009/0076559 A1 | 3/2009 | Libbus et al. |
| 2009/0088652 A1 | 4/2009 | Tremblay |
| 2009/0112116 A1 | 4/2009 | Lee et al. |
| 2009/0131759 A1 | 5/2009 | Sims et al. |
| 2009/0156908 A1 | 6/2009 | Belalcazar et al. |
| 2009/0216132 A1 | 8/2009 | Orbach |
| 2009/0270708 A1 | 10/2009 | Shen et al. |
| 2009/0270747 A1 | 10/2009 | Van Dam et al. |
| 2009/0292194 A1 | 11/2009 | Libbus et al. |
| 2010/0007413 A1 | 1/2010 | Herleikson et al. |
| 2010/0022897 A1 | 1/2010 | Parker et al. |
| 2010/0056881 A1 | 3/2010 | Libbus et al. |
| 2010/0081913 A1 | 4/2010 | Cross et al. |
| 2010/0174229 A1 | 7/2010 | Hsu et al. |
| 2010/0177100 A1 | 7/2010 | Carnes et al. |
| 2010/0185063 A1 | 7/2010 | Bardy |
| 2010/0185076 A1 | 7/2010 | Jeong et al. |
| 2010/0191154 A1 | 7/2010 | Berger et al. |
| 2010/0191310 A1 | 7/2010 | Bly |
| 2010/0223020 A1 | 9/2010 | Goetz |
| 2010/0234715 A1 | 9/2010 | Shin et al. |
| 2010/0234716 A1 | 9/2010 | Engel |
| 2010/0280366 A1 | 11/2010 | Arne et al. |
| 2010/0312188 A1 | 12/2010 | Robertson et al. |
| 2010/0324384 A1 | 12/2010 | Moon et al. |
| 2011/0021937 A1 | 1/2011 | Hugh et al. |
| 2011/0054286 A1 | 3/2011 | Crosby et al. |
| 2011/0060215 A1 | 3/2011 | Tupin et al. |
| 2011/0066041 A1 | 3/2011 | Pandia et al. |
| 2011/0077497 A1 | 3/2011 | Oster et al. |
| 2011/0105861 A1 | 5/2011 | Derchak et al. |
| 2011/0144470 A1 | 6/2011 | Mazar et al. |
| 2011/0160548 A1 | 6/2011 | Forster |
| 2011/0224564 A1 | 9/2011 | Moon et al. |
| 2011/0237922 A1 | 9/2011 | Parker, III et al. |
| 2011/0237924 A1 | 9/2011 | McGusty et al. |
| 2011/0245699 A1 | 10/2011 | Snell et al. |
| 2011/0245711 A1 | 10/2011 | Katra et al. |
| 2011/0288605 A1 | 11/2011 | Kaib et al. |
| 2012/0003933 A1 | 1/2012 | Baker et al. |
| 2012/0029306 A1 | 2/2012 | Paquet et al. |
| 2012/0029315 A1 | 2/2012 | Raptis et al. |
| 2012/0029316 A1 | 2/2012 | Raptis et al. |
| 2012/0035432 A1 | 2/2012 | Katra et al. |

(56) References Cited

U.S. PATENT DOCUMENTS

| | | |
|---|---|---|
| 2012/0059668 A1 | 3/2012 | Baldock et al. |
| 2012/0078127 A1 | 3/2012 | McDonald et al. |
| 2012/0088998 A1 | 4/2012 | Bardy et al. |
| 2012/0088999 A1 | 4/2012 | Bishay et al. |
| 2012/0089000 A1 | 4/2012 | Bishay et al. |
| 2012/0089001 A1 | 4/2012 | Bishay et al. |
| 2012/0089037 A1 | 4/2012 | Bishay et al. |
| 2012/0089412 A1 | 4/2012 | Bishay et al. |
| 2012/0089417 A1 | 4/2012 | Bardy et al. |
| 2012/0095352 A1 | 4/2012 | Tran |
| 2012/0101358 A1 | 4/2012 | Boettcher et al. |
| 2012/0101396 A1 | 4/2012 | Solosko et al. |
| 2012/0165645 A1 | 6/2012 | Russel et al. |
| 2012/0306662 A1 | 6/2012 | Vosch et al. |
| 2012/0172695 A1 | 7/2012 | Ko et al. |
| 2012/0220835 A1 | 8/2012 | Chung |
| 2012/0232929 A1 | 9/2012 | Experton |
| 2012/0238910 A1 | 9/2012 | Nordstrom |
| 2012/0253847 A1 | 10/2012 | Dell'Anno et al. |
| 2012/0302906 A1 | 11/2012 | Felix et al. |
| 2012/0330126 A1 | 12/2012 | Hoppe et al. |
| 2013/0041272 A1 | 2/2013 | Javier et al. |
| 2013/0077263 A1 | 3/2013 | Oleson et al. |
| 2013/0079611 A1 | 3/2013 | Besko |
| 2013/0085347 A1 | 4/2013 | Manicka et al. |
| 2013/0085403 A1 | 4/2013 | Gunderson et al. |
| 2013/0087609 A1 | 4/2013 | Nichol et al. |
| 2013/0096395 A1 | 4/2013 | Katra et al. |
| 2013/0116533 A1 | 5/2013 | Lian et al. |
| 2013/0123651 A1 | 5/2013 | Bardy |
| 2013/0158361 A1 | 6/2013 | Bardy |
| 2013/0197380 A1 | 8/2013 | Oral et al. |
| 2013/0225963 A1 | 8/2013 | Kodandaramaiah et al. |
| 2013/0225966 A1 | 8/2013 | Macia Barber et al. |
| 2013/0231947 A1 | 9/2013 | Shusterman |
| 2013/0243105 A1 | 9/2013 | Lei et al. |
| 2013/0274584 A1 | 10/2013 | Finlay et al. |
| 2013/0275158 A1 | 10/2013 | Fahey |
| 2013/0324809 A1 | 12/2013 | Lisogurski et al. |
| 2013/0324855 A1 | 12/2013 | Lisogurski et al. |
| 2013/0324856 A1 | 12/2013 | Lisogurski et al. |
| 2013/0325081 A1 | 12/2013 | Karst et al. |
| 2013/0325359 A1 | 12/2013 | Jarverud et al. |
| 2013/0331665 A1 | 12/2013 | Libbus et al. |
| 2013/0338448 A1 | 12/2013 | Libbus et al. |
| 2013/0338472 A1 | 12/2013 | Macia Barber et al. |
| 2014/0012154 A1 | 1/2014 | Mazar et al. |
| 2014/0056452 A1 | 2/2014 | Moss et al. |
| 2014/0088399 A1 | 3/2014 | Lian et al. |
| 2014/0107509 A1 | 4/2014 | Banet et al. |
| 2014/0140359 A1 | 5/2014 | Kalevo et al. |
| 2014/0180027 A1 | 6/2014 | Buller |
| 2014/0189928 A1 | 7/2014 | Oleson et al. |
| 2014/0194760 A1 | 7/2014 | Albert |
| 2014/0206977 A1 | 7/2014 | Bahney et al. |
| 2014/0214134 A1* | 7/2014 | Peterson ............ A61H 39/002 607/62 |
| 2014/0215246 A1 | 7/2014 | Lee et al. |
| 2014/0249852 A1 | 9/2014 | Proud |
| 2014/0296651 A1 | 10/2014 | Stone |
| 2014/0343390 A1 | 11/2014 | Berzowska et al. |
| 2014/0358193 A1 | 12/2014 | Lyons et al. |
| 2014/0364756 A1 | 12/2014 | Brockway et al. |
| 2015/0048836 A1 | 2/2015 | Guthrie et al. |
| 2015/0065842 A1 | 3/2015 | Lee et al. |
| 2015/0142090 A1* | 5/2015 | Duijsens ............ A61N 1/05 607/116 |
| 2015/0164349 A1 | 6/2015 | Gopalakrishnan et al. |
| 2015/0165211 A1 | 6/2015 | Naqvi et al. |
| 2015/0177175 A1 | 6/2015 | Elder et al. |
| 2015/0250422 A1 | 9/2015 | Bay |
| 2015/0257670 A1 | 9/2015 | Ortega et al. |
| 2015/0305676 A1 | 11/2015 | Shoshani |
| 2015/0359489 A1 | 12/2015 | Baudenbacher et al. |
| 2016/0135746 A1 | 5/2016 | Kumar et al. |
| 2016/0144190 A1 | 5/2016 | Cao et al. |
| 2016/0144192 A1 | 5/2016 | Sanghera et al. |
| 2016/0217691 A1 | 7/2016 | Kadobayashi et al. |
| 2016/0235318 A1 | 8/2016 | Sarkar |
| 2017/0112399 A1 | 4/2017 | Brisben et al. |
| 2017/0156592 A1 | 6/2017 | Fu |
| 2017/0281032 A1 | 10/2017 | Weinberg et al. |
| 2017/0366921 A1* | 12/2017 | Pflugh ............ H04W 4/70 |
| 2018/0078771 A1* | 3/2018 | Koop ............ A61B 5/686 |
| 2019/0021671 A1 | 1/2019 | Kumar et al. |
| 2019/0059763 A1 | 2/2019 | Shakur et al. |

FOREIGN PATENT DOCUMENTS

| | | |
|---|---|---|
| EP | 2438851 | 4/2012 |
| EP | 2438852 | 4/2012 |
| EP | 2465415 | 6/2012 |
| EP | 2589333 | 5/2013 |
| JP | H06319711 | 11/1994 |
| JP | H11188015 | 7/1999 |
| JP | 2004129788 | 4/2004 |
| JP | 2007082938 | 4/2007 |
| JP | 2009219554 | 10/2009 |
| WO | 199852463 | 11/1998 |
| WO | 00/78213 | 12/2000 |
| WO | 2003032192 | 4/2003 |
| WO | 2006009767 | 1/2006 |
| WO | 2006014806 | 2/2006 |
| WO | 2007066270 | 6/2007 |
| WO | 2007092543 | 8/2007 |
| WO | 2008010216 | 1/2008 |
| WO | 2008057884 | 5/2008 |
| WO | 2008092098 | 7/2008 |
| WO | 2009036306 | 3/2009 |
| WO | 2009036313 | 3/2009 |
| WO | 2009036327 | 3/2009 |
| WO | 2009112976 | 9/2009 |
| WO | 2009112978 | 9/2009 |
| WO | 2009112979 | 9/2009 |
| WO | 2009142975 | 11/2009 |
| WO | 2010066507 | 6/2010 |
| WO | 2010105045 | 6/2010 |
| WO | 2011047207 | 4/2011 |
| WO | 2012140559 | 10/2012 |
| WO | 2012146957 | 11/2012 |
| WO | 2017072250 | 5/2017 |

OTHER PUBLICATIONS

Alivecor, URL <http://www.businesswire.com/news/home/20121203005545/en/AliveCor%E2%80%99s-Heart-Monitor-iPhone-Receives-FDA-Clearance#.U7rtq7FVTyF> (Dec. 3, 2012).

Bharadwaj et al., Techniques for Accurate ECG signal processing, EE Times, URL <www.eetimes.com/document.asp?doc_id=1278571> (Feb. 14, 2011).

Chen et al. "Monitoring Body Temperature of Newborn Infants at Neonatal Intensive Care Units Using Wearable Sensors," BodyNets 2010, Corfu Island, Greece. Sep. 10-12, 1210.

Epstein, Andrew E. et al.; ACC/AHA/HRS 2008 Guidelines for Device-Based Therapy of Cardiac Rhythm Abnormalities. J. Am. Coll. Cardiol. 2008; 51; el-e62, 66 Pgs.

Fitbit Tracker, URL <http://www.fitbit.com/> (Web page cached on Sep. 10, 2008.).

Smith, Jawbone up, URL <http://www.businessinsider.com/fitbit-flex-vs-jawbone-up-2013-5?op=1> (Jun. 1, 2013).

Kligfield, Paul et al., Recommendations for the Standardization and Interpretation of the Electrocardiogram: Part I. J.Am.Coll. Cardiol; 2007; 49; 1109-27, 75 Pgs.

Lauren Gravitz, "When Your Diet Needs a Band-Aid," Technology Review, MIT. (May 1, 2009).

Lieberman, Jonathan, "How Telemedicine Is Aiding Prompt ECG Diagnosis in Primary Care," British Journal of Community Nursing, vol. 13, No. 3, Mar. 1, 2008 (Mar. 1, 2008), pp. 123-126, XP009155082, ISSN: 1462-4753.

McManus et al., "A Novel Application for the Detection of an Irregular Pulse using an iPhone 4S in Patients with Atrial Fibrillation," vol. 10(3), pp. 315-319 (Mar. 2013.).

(56) References Cited

OTHER PUBLICATIONS

Nike+ Fuel Band, URL <http://www.nike.com/us/en_us/c/nikeplus-fuelband> (Web page cached on Jan. 11, 2013.).
P. Libby et al.,"Braunwald's Heart Disease—A Textbook of Cardiovascular Medicine," Chs. 11, pp. 125-148 and 12, pp. 149-193 (8th ed. 2008), American Heart Association.
Initial hands-on with Polar Loop activity tracker, URL <http://www.dcrainmaker.com/2013/09/polar-loop-firstlook.html> (Sep. 17, 2013).
Seifert, Dan, Samsung dives into fitness wearable with the Gear Fit/ The Verge, URL <http://www.theverge.com/2014/2/24/5440310/samsung-dives-into-fitness-wearables-with-the-gear-fit> (Feb. 24, 2014).
Soper, Taylor, Samsung's new Galaxy S5 flagship phone has fingerprint reader, heart rate monitor, URL <http://www.geekwire.com/2014/samsung-galaxy-s5-fingerprint> (Feb. 24, 2014).
Dolcourt, See the Samsung Galaxy S5's Heart rate monitor in action, URL <http://www.cnet.com/news/see-the-samsung-galaxy-s5s-heart-rate-monitor-in-action> (Feb. 25, 2014).
Sittig et al., "A Computer-Based Outpatient Clinical Referral System," International Journal of Medical Informatics, Shannon, IR, vol. 55, No. 2, Aug. 1, 1999, pp. 149-158, XO004262434, ISSN: 1386-5056(99)00027-1.
Sleepview, URL <http://www.clevemed.com/sleepview/overview.shtml> (Web page cached on Sep. 4, 2011).
Actigraphy/ Circadian Rhythm SOMNOwatch, URL <http://www.somnomedics.eu/news-events/publications/somnowatchtm.html> (Web page cached on Jan. 23, 2010).
Zio Event Card, URL <http://www.irhythmtech.com/zio-solution/zio-event/> (Web page cached on Mar. 11, 2013.).
Zio Patch System, URL <http://www.irhythmtech.com/zio-solution/zio-system/index.html> (Web page cached on Sep. 8, 2011).
Saadi et al. "Heart Rhythm Analysis Using ECG Recorded With a Novel Sternum Based Patch Technology—A Pilot Study." Cardio technix 2013—Proceedings of the International Congress on Cardiovascular Technologies, Sep. 20, 2013.
Anonymous. "Omegawave Launches Consumer App 2.0 in U.S. Endurance Sportswire—Endurance Sportswire." Jul. 11, 2013. URL:http://endurancesportswire.com/omegawave-launches-consumer-app-2-0-in-u-s/.
Chan et al. "Wireless Patch Sensor for Remote Monitoring of Heart Rate, Respiration, Activity, and Falls." pp. 6115-6118. 2013 35th Annual International Conference of the IEEE Engineering in Medical and Biology Society.
Wei et al. "A Stretchable and Flexible System for Skin-Mounted Measurement of Motion Tracking and Physiological Signals." pp. 5772-5775. 2014 36th Annual International Conference of the IEEE Engineering in Medicine and Biology Society. Aug. 26, 2014.
Daoud et al. "Fall Detection Using Shimmer Technology and Multiresolution Analysis." Aug. 2, 2013. URL: https://decibel.ni.com/content/docs/DOC-26652.
Libbus. "Adherent Cardiac Monitor With Wireless Fall Detection for Patients With Unexplained Syncope." Abstracts of the First AMA-IEEE Medical Technology Conference on Individualized Healthcare. May 22, 2010.
Duttweiler et al., "Probability Estimation in Arithmetic and Adaptive-Huffman Entropy Coders," IEEE Transactions on Image Processing. vol. 4, No. 3, Mar. 1, 1995, pp. 237-246.
Gupta et al., "An ECG Compression Technique for Telecardiology Application," India Conference (INDICON), 2011 Annual IEEE, Dec. 16, 2011, pp. 1-4.
Nave et al., "ECG Compression Using Long-Term Prediction," IEEE Transactions on Biomedical Engineering, IEEE Service Center, NY, USA, vol. 40, No. 9, Sep. 1, 1993, pp. 877-885.
Skretting et al., "Improved Huffman Coding Using Recursive Splitting," NORSIG, Jan. 1, 1999.
A Voss et al., "Linear and Nonlinear Methods for Analyses of Cardiovascular Variability in Bipolar Disorders," Bipolar Disorders, votl. 8, No. 5p1, Oct. 1, 2006, pp. 441-452, XP55273826, DK ISSN: 1398-5647, DOI: 10.1111/i.1399-5618.2006.00364.x.
Varicrad-Kardi Software User's Manual Rev. 1.1, Jul. 8, 2009 (Jul. 8, 2009), XP002757888, retrieved from the Internet: URL:http://www.ehrlich.tv/KARDiVAR-Software.pdf [retrieved on May 20, 2016].
Vedapulse UK, Jan. 1, 2014 (Jan. 1, 2014), XP002757887, Retrieved from the Internet: URL:http://www.vedapulseuk.com/diagnostic/ [retrieved on May 19, 2016].
http://www.originlab.com/origin#Data_Exploration 2015.
https://web.archive.org/web/20130831204020/http://www.biopac.com/research.asp?CatID=37&Main=Software (Aug. 2013).
http://www.gtec.at/Products/Software/g.BSanalyze-Specs-Features (2014).
ADINSTRUMENTS:ECG Analysis Module for LabChart & PowerLab, 2008.
BIOPAC Systems, Inc. #AS148-Automated ECG Analysis , Mar. 24, 2006.
Health Research—Hexoskin Biometric Shirt | Hexoskin URL:http://www.hexoskin.com/pages/health-research (Web page cached on Dec. 2, 2014).
Jacob Kastrenakes, "Apple Watch uses four sensors to detect your pulse," Sep. 9, 2014. URL: http://www.theverge.com/2014/9/9/6126991/apple-watch-four-back-sensors-detect-activity.
Nicole Lee, "Samsung Gear S review: an ambitious and painfully flawed smartwatch," Dec. 1, 2014. URL: http://www.engadget.com/2014/12/01/samsung-gear-s-review/.
G. G. Ivanov, "HRV Analysis Under the Usage of Different Electrocardiopraphy Systems," Apr. 15, 2008 (Apr. 15, 2008), XP55511209, Retrieved from the Internet: URL:http://www.drkucera.eu/upload_doc/hrv_analysis_(methodical_recommendations).pdf [retrieved on Oct. 1, 2018].
Pranav Rajpurkar et al. "Cardiologist-Level Arrhythmia Detection with Convolutional Neural Networks,"arxiv.org, Cornell University Library, 201 Olin Library Cornell University Ithaca, NY 14853, Jul. 6, 2017 (Jul. 6, 2017), XP080774895.
Pourbabaee Bahareh et al. "Feature Learning with Deep Convolutional Neural Networks for Screening Patients with Paroxysmal Atrial Fibrillation," 2016 Neural Networks (IJCNN), 2016 International Joint Conference on Neural Networks (IJCNN), IEEE, Jul. 24, 2016 (Jul. 24, 2016), pp. 5057-5064, XP032992832, DOI: 10.1109/IJCNN.2016.7727866.
Xiong Zhaohan et al. "Robust ECG Signal Classification for Detection of Atrial Fibrillation Using a Novel Neural Network," 2017 Computing in Cardiology (CinC), CCAL, Sep. 24, 2017 (Sep. 24, 2017), pp. 1-4, XP033343575, DOI: 10.22489/CinC.2017.066-138.

* cited by examiner (a)

(b)

SUBCUTANEOUS INSERTABLE ELECTROCARDIOGRAPHY MONITOR

CROSS-REFERENCE TO RELATED APPLICATION

This U.S. patent application is a continuation-in-part of U.S. patent application Ser. No. 15/905,715, filed Feb. 26, 2018, which is a continuation of U.S. Pat. No. 9,901,274, issued Feb. 27, 2018, which is a continuation of U.S. Pat. No. 9,545,204, issued Jan. 17, 2017, which claims priority under 35 U.S.C. § 119(e) to U.S. Provisional Patent application Ser. No. 61/882,403, filed Sep. 25, 2013, the disclosure of which is incorporated by reference; this present non-provisional patent application is also a continuation-in-part of U.S. patent application Ser. No. 15/832,385, filed Dec. 5, 2017, pending, the disclosure of which is incorporated by reference.

FIELD

This application relates in general to electrocardiographic monitoring and, in particular, to a subcutaneous insertable electrocardiography monitor.

BACKGROUND

The heart emits electrical signals as a by-product of the propagation of the action potentials that trigger depolarization of heart fibers. An electrocardiogram (ECG) measures and records such electrical potentials to visually depict the electrical activity of the heart over time. Conventionally, a standardized set format 12-lead configuration is used by an ECG machine to record cardiac electrical signals from well-established traditional chest locations. Electrodes at the end of each lead are placed on the skin over the anterior thoracic region of the patient's body to the lower right and to the lower left of the sternum, on the left anterior chest, and on the limbs. Sensed cardiac electrical activity is represented by PQRSTU waveforms that can be interpreted post-ECG recordation to derive heart rate and physiology. The P-wave represents atrial electrical activity. The QRSTU components represent ventricular electrical activity.

An ECG is a tool used by physicians to diagnose heart problems and other potential health concerns. An ECG is a snapshot of heart function, typically recorded over 12 seconds, that can help diagnose rate and regularity of heartbeats, effect of drugs or cardiac devices, including pacemakers and implantable cardioverter-defibrillators (ICDs), and whether a patient has heart disease. ECGs are used in-clinic during appointments, and, as a result, are limited to recording only those heart-related aspects present at the time of recording. Sporadic conditions that may not show up during a spot ECG recording require other means to diagnose them. These disorders include fainting or syncope; rhythm disorders, such as tachyarrhythmias and bradyarrhythmias; apneic episodes; and other cardiac and related disorders. Thus, an ECG only provides a partial picture and can be insufficient for complete patient diagnosis of many cardiac disorders.

Diagnostic efficacy can be improved, when appropriate, through the use of long-term extended ECG monitoring. Recording sufficient ECG, that is of a quality sufficient to be useful in arrhythmia diagnosis, and related physiology over an extended period is challenging, and often essential to enabling a physician to identify events of potential concern. A 30-day observation day period is considered the "gold standard" of ECG monitoring, yet achieving a 30-day observation day period has proven unworkable because such ECG monitoring systems are arduous to employ, cumbersome to the patient, and excessively costly. Ambulatory monitoring in-clinic is implausible and impracticable. Nevertheless, if a patient's ECG could be recorded in an ambulatory setting, thereby allowing the patient to engage in activities of daily living, the chances of acquiring meaningful information and capturing an abnormal event while the patient is engaged in normal activities becomes more likely to be achieved.

For instance, the long-term wear of dermal ECG electrodes is complicated by skin irritation and the inability ECG electrodes to maintain continual skin contact after a day or two. Moreover, time, dirt, moisture, and other environmental contaminants, as well as perspiration, skin oil, and dead skin cells from the patient's body, can get between an ECG electrode, the non-conductive adhesive used to adhere the ECG electrode, and the skin's surface. All of these factors adversely affect electrode adhesion and the quality of cardiac signal recordings. Furthermore, the physical movements of the patient and their clothing impart various compressional, tensile, and torsional forces on the contact point of an ECG electrode, especially over long recording times, and an inflexibly fastened ECG electrode will be prone to becoming dislodged. Notwithstanding the cause of electrode dislodgment, depending upon the type of ECG monitor employed, precise re-placement of a dislodged ECG electrode maybe essential to ensuring signal capture at the same fidelity. Moreover, dislodgment may occur unbeknownst to the patient, making the ECG recordings worthless. Further, some patients may have skin that is susceptible to itching or irritation, and the wearing of ECG electrodes can aggravate such skin conditions. Thus, a patient may want or need to periodically remove or replace ECG electrodes during a long-term ECG monitoring period, whether to replace a dislodged electrode, reestablish better adhesion, alleviate itching or irritation, allow for cleansing of the skin, allow for showering and exercise, or for other purpose. Such replacement or slight alteration in electrode location actually facilitates the goal of recording the ECG signal for long periods of time.

While subcutaneous ECG monitors can perform monitoring for an extended period of time, up to three years, such subcutaneous ECG monitors, because of their small size, have greater problems of demonstrating a clear and dependable P-wave. The issues related to a tiny atrial voltage are exacerbated by the small size of insertable cardiac monitors (ICMs), the signal processing limits imposed upon them by virtue of their reduced electrode size, and restricted inter-electrode spacing. Conventional subcutaneous ICMs, as well as most conventional surface ECG monitors, are notorious for poor visualization of the P-wave, which remains the primary reason that heart rhythm disorders cannot precisely be identified today from ICMs. Furthermore, even when physiologically present, the P-wave may not actually appear on an ECG because the P-wave's visibility is strongly dependent upon the signal capturing ability of the ECG recording device's sensing circuitry. This situation is further influenced by several factors, including electrode configuration, electrode surface areas and shapes, inter-electrode spacing; where the electrodes are placed on or within the body relative to the heart's atria. Further, the presence or absence of ambient noise and the means to limit the ambient noise is a key aspect of whether the low amplitude atrial signal can be seen.

Conventional ICMs are often used after diagnostic measures when dermal ECG monitors fail to identify a suspected arrhythmia. Consequently, when a physician is strongly suspicious of a serious cardiac rhythm disorder that may have caused loss of consciousness or stroke, for example, the physician will often proceed to the insertion of an ICM under the skin of the thorax. Although traditionally, the quality of the signal is limited with ICMs with respect to identifying the P-wave, the duration of monitoring is hoped to compensate for poor P-wave recording. This situation has led to a dependence on scrutiny of R-wave behavior, such as RR interval (R-wave-to-R-wave interval) behavior, often used as a surrogate for diagnosing atrial fibrillation, a potential cause of stroke. To a limited extent, this approach has some degree of value. Nevertheless, better recording of the P-wave would result in a significant diagnostic improvement, not only in the case of atrial fibrillation, but in a host of other rhythm disorders that can result in syncope or loss of consciousness, like VT or heart block.

The P-wave is the most difficult ECG signal to capture by virtue of originating in the low tissue mass atria and having both low voltage amplitude and relatively low frequency content. Notwithstanding these physiological constraints, ICMs are popular, albeit limited in their diagnostic yield. The few ICMs that are commercially available today, including the Reveal LINQ ICM, manufactured by Medtronic, Inc., Minneapolis, Minn., the BioMonitor 2 (AF and S versions), manufactured by Biotronik SE & Co. KG, Berlin, Germany, and the Abbott Confirm Rx ICM, manufactured by Abbott Laboratories, Chicago, Ill., all are uniformly limited in their abilities to clearly and consistently sense, record, and deliver the P-wave.

Typically, the current realm of ICM devices use a loop recorder where cumulative ECG data lasting for around an hour is continually overwritten unless an episode of preprogrammed interest occurs or a patient marker is manually triggered. The limited temporal window afforded by the recordation loop is yet another restriction on the evaluation of the P-wave, and related cardiac morphologies, and further compromises diagnostic opportunities.

For instance, Medtronic's Reveal LINQ ICM delivers long-term subcutaneous ECG monitoring for up to three years, depending on programming. The monitor is able to store up to 59 minutes of ECG data, include up to 30 minutes of patient-activated episodes, 27 minutes of automatically detected episodes, and two minutes of the longest atrial fibrillation (AF) episode stored since the last interrogation of the device. The focus of the device is more directed to recording duration and programming options for recording time and patient interactions rather than signal fidelity. The Reveal LINQ ICM is intended for general purpose ECG monitoring and lacks an engineering focus on P-wave visualization. Moreover, the device's recording circuitry is intended to secure the ventricular signal by capturing the R-wave, and is designed to accommodate placement over a broad range of subcutaneous implantation sites, which is usually sufficient if one is focused on the R-wave given its amplitude and frequency content, but of limited value in capturing the low-amplitude, low-frequency content P-wave. Finally, electrode spacing, surface areas, and shapes are dictated (and limited) by the physical size of the monitor's housing which is quite small, an aesthetic choice, but unrealistic with respect to capturing the P-wave.

Similar in design is the titanium housing of Biotronik's BioMonitor 2 but with a flexible silicone antenna to mount a distal electrode lead, albeit of a standardized length. This standardized length mollifies, in one parameter only, the concerns of limited inter-electrode spacing and its curbing effect on securing the P-wave. None of the other factors related to P-wave signal revelation are addressed. Therefore the quality of sensed P-waves reflects a compromise caused by closely-spaced poles that fail to consistently preserve P-wave fidelity, with the reality of the physics imposed problems of signal-to-noise ratio limitations remaining mostly unaddressed.

Therefore, a need remains for a continuously recording long-term ICM capable of conducting a long-term ECG monitoring and that is attuned for recording low amplitude cardiac action potential propagation from the atria, that is, the P-wave, for accurate arrhythmia event capture and subsequent diagnosis.

SUMMARY

Long-term electrocardiographic and physiological monitoring over a period lasting up to several years in duration can be provided through a continuously-recording subcutaneous insertable cardiac monitor (ICM), such as one described in commonly-owned U.S. patent application Ser. No. 15/832,385, filed Dec. 5, 2017, pending, the disclosure of which is incorporated by reference. The sensing circuitry and the physical layout of the electrodes are specifically optimized to capture electrical signals from the propagation of low amplitude, relatively low frequency content cardiac action potentials, particularly the P-waves that are generated during atrial activation. In general, the ICM is intended to be implanted centrally and positioned axially and slightly to either the left or right of the sternal midline in the parasternal region of the chest, with at least one of the ECG sensing electrodes of the ICM being disposed for being positioned in a region overlying the sternum or adjacent to the sternum in the parasternal regions when the housing has been implanted.

In one embodiment, a subcutaneous insertable electrocardiography (ECG) monitor is provided. The monitor includes an implantable housing included of a biocompatible material that is suitable for implantation within a living body in at least one of the sternal midline and the parasternal region of the chest of the body; at least a pair of ECG sensing electrodes provided on a ventral surface and on opposite ends of the implantable housing operatively placed to facilitate sensing in closest proximity to the low amplitude, low frequency content cardiac action potentials that are generated during atrial activation, the electrodes being disposed for being positioned in a region overlying the sternum or adjacent to the sternum in the parasternal region on a patient's chest when the housing has been implanted; and electronic circuitry provided within the housing assembly including a low power microcontroller operable to execute under modular micro program control as specified in firmware, an ECG front end circuit interfaced to the microcontroller and configured to capture the cardiac action potentials sensed by the pair of ECG sensing electrodes which are output as ECG signals, and non-volatile memory electrically interfaced with the microcontroller and operable to continuously store samples of the ECG signals.

In a further embodiment, a rectangular subcutaneous insertable electrocardiography monitor is provided. The monitor includes a hermetically sealed implantable housing defining a rectangular shape with rounded edges and included of a biocompatible material that is suitable for implantation within a living body of a patient in at least one of the sternal midline and the parasternal region of the chest of the body; at least a pair of ECG sensing electrodes provided on a ventral surface and on opposite ends of the implantable housing operatively placed to facilitate sensing in closest proximity to the low amplitude, low frequency content cardiac action potentials that are generated during atrial activation, one of the electrodes being disposed for being positioned in a region overlying the inferior sternum or adjacent to the inferior sternum in the parasternal region the other of the electrodes being disposed for being positioned in the region overlying the superior sternum or adjacent to the superior sternum in the parasternal region of the patient's chest when the housing has been implanted; and electronic circuitry provided within the housing assembly including a low power microcontroller operable to execute under modular micro program control as specified in firmware, an ECG front end circuit interfaced to the microcontroller and configured to capture the cardiac action potentials sensed by the pair of ECG sensing electrodes which are output as ECG signals, and non-volatile memory electrically interfaced with the microcontroller and operable to continuously store samples of the ECG signals.

The foregoing aspects enhance ECG monitoring performance and quality facilitating long-term ECG recording, critical to accurate arrhythmia diagnosis.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

DETAILED DESCRIPTION

Figure 1:
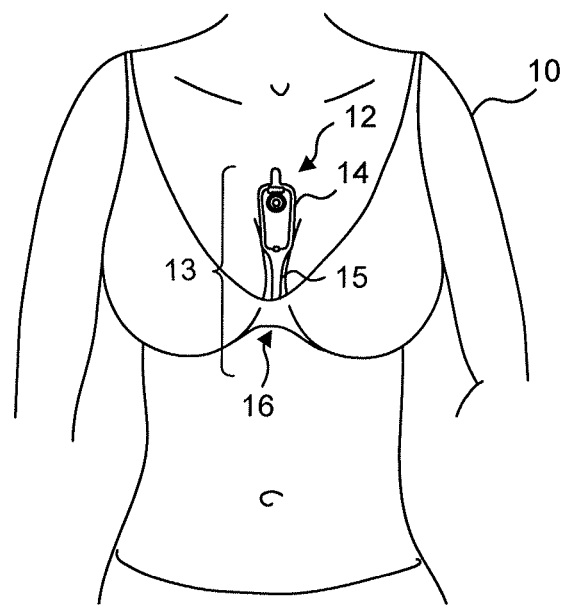
FIGS. 1 and 2 are diagrams showing, by way of examples, an extended wear electrocardiography monitor, including an extended wear electrode patch in accordance with one embodiment, respectively fitted to the sternal region of a female patient and a male patient.
Figure 2:
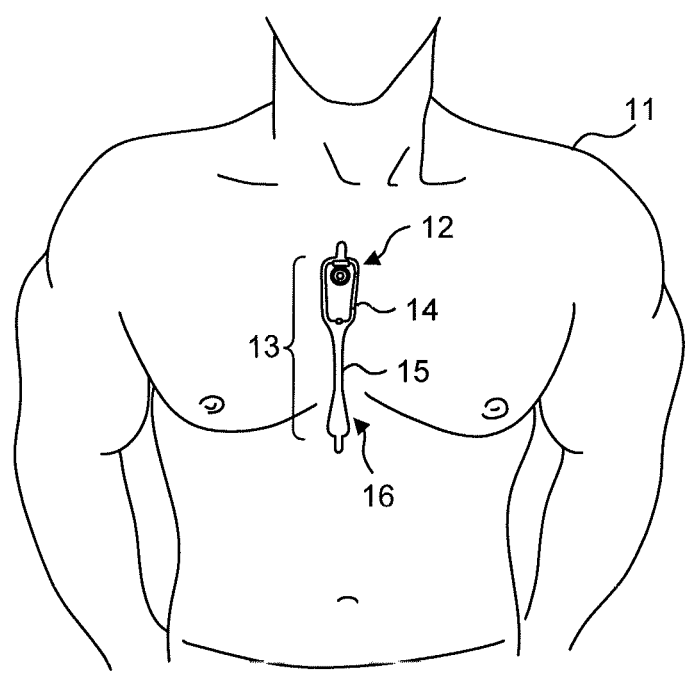

Physiological monitoring can be provided through a wearable monitor that includes two components, a flexible extended wear electrode patch and a removable reusable monitor recorder. FIGS. 1 and 2 are diagrams showing, by way of examples, an extended wear electrocardiography monitor 12, including an extended wear electrode patch 15 in accordance with one embodiment, respectively fitted to the sternal region of a female patient 10 and a male patient 11. The wearable monitor 12 sits centrally (in the midline) on the patient's chest along the sternum 13 oriented top-to-bottom with the monitor recorder 14 preferably situated towards the patient's head. The electrode patch 15 is shaped to fit comfortably and conformal to the contours of the patient's chest approximately centered on the sternal midline 16 (or immediately to either side of the sternum 13). The distal end of the electrode patch 15 extends towards the Xiphoid process and, depending upon the patient's build, may straddle the region over the Xiphoid process. The proximal end of the electrode patch 15, located under the monitor recorder 14, is below the manubrium and, depending upon patient's build, may straddle the region over the manubrium.

The placement of the wearable monitor 12 in a location at the sternal midline 16 (or immediately to either side of the sternum 13) significantly improves the ability of the wearable monitor 12 to cutaneously sense cardiac electric signals, particularly the P-wave (or atrial activity) and, to a lesser extent, the QRS interval signals in the ECG waveforms that indicate ventricular activity. The sternum 13 overlies the right atrium of the heart and the placement of the wearable monitor 12 in the region of the sternal midline 13 puts the ECG electrodes of the electrode patch 15 in a location better adapted to sensing and recording P-wave signals than other placement locations, say, the upper left pectoral region. In addition, placing the lower or inferior pole (ECG electrode) of the electrode patch 15 over (or near) the Xiphoid process facilitates sensing of right ventricular activity and provides superior recordation of the QRS interval.

Figure 3:
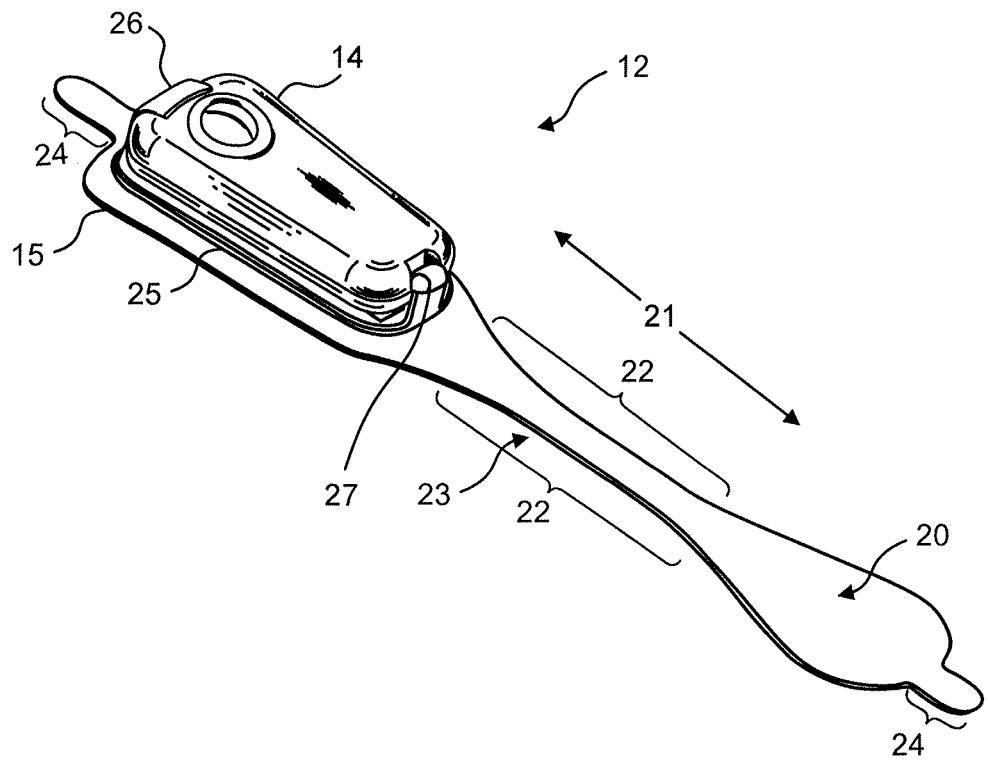
FIG. 3 is a perspective view showing an extended wear electrode patch in accordance with one embodiment with a monitor recorder inserted.

During use, the electrode patch 15 is first adhesed to the skin along the sternal midline 16 (or immediately to either side of the sternum 13). A monitor recorder 14 is then snapped into place on the electrode patch 15 to initiate ECG monitoring. FIG. 3 is a perspective view showing an extended wear electrode patch 15 in accordance with one embodiment with a monitor recorder 14 inserted. The body of the electrode patch 15 is preferably constructed using a flexible backing 20 formed as an elongated strip 21 of wrap knit or similar stretchable material about 145 mm long and 32 mm at the widest point with a narrow longitudinal mid-section 23 evenly tapering inward from both sides. A pair of cut-outs 22 between the distal and proximal ends of the electrode patch 15 create a narrow longitudinal midsection 23 or "isthmus" and defines an elongated "hourglass"-like shape, when viewed from above, such as described in commonly-assigned U.S. Design Pat. No. D744,659, issued Dec. 1, 2015, the disclosure of which is incorporated by reference. The upper part of the "hourglass" is sized to allow an electrically non-conductive receptacle 25, sits on top of the outward-facing surface of the electrode patch 15, to be affixed to the electrode patch 15 with an ECG electrode placed underneath on the patient-facing underside, or contact, surface of the electrode patch 15; the upper part of the "hourglass" has a longer and wider profile than the lower part of the "hourglass," which is sized primarily to allow just the placement of an ECG electrode.

The electrode patch 15 incorporates features that significantly improve wearability, performance, and patient comfort throughout an extended monitoring period. During wear, the electrode patch 15 is susceptible to pushing, pulling, and torqueing movements, including compressional and torsional forces when the patient bends forward, and tensile and torsional forces when the patient leans backwards. To counter these stress forces, the electrode patch 15 incorporates crimp and strain reliefs, as further described infra respectively with reference to FIGS. 4 and 5. In addition, the cut-outs 22 and longitudinal midsection 23 help minimize interference with and discomfort to breast tissue, particularly in women (and gynecomastic men). The cut-outs 22 and longitudinal midsection 23 allow better conformity of the electrode patch 15 to sternal bowing and to the narrow isthmus of flat skin that can occur along the bottom of the intermammary cleft between the breasts, especially in buxom women. The cut-outs 22 and longitudinal midsection 23 help the electrode patch 15 fit nicely between a pair of female breasts in the intermammary cleft. In one embodiment, the cut-outs 22 can be graduated to form the longitudinal midsection 23 as a narrow in-between stem or isthmus portion about 7 mm wide. In a still further embodiment, tabs 24 can respectively extend an additional 8 mm to 12 mm beyond the distal and proximal ends of the flexible backing 20 to facilitate purchase when adhering the electrode patch 15 to or removing the electrode patch 15 from the sternum 13. These tabs preferably lack adhesive on the underside, or contact, surface of the electrode patch 15. Still other shapes, cut-outs and conformities to the electrode patch 15 are possible.

The monitor recorder 14 removably and reusably snaps into an electrically non-conductive receptacle 25 during use. The monitor recorder 14 contains electronic circuitry for recording and storing the patient's electrocardiography as sensed via a pair of ECG electrodes provided on the electrode patch 15, such as described in commonly-assigned U.S. Pat. No. 9,730,593, issued Aug. 15, 2017, the disclosure of which is incorporated by reference. The circuitry includes a microcontroller, flash storage, ECG signal processing, analog-to-digital conversion (where applicable), and an external interface for coupling to the electrode patch 15 and to a download station for stored data download and device programming. The monitor recorder 14 also includes external patient-interfaceable controls, such as a push button to facilitate event marking and a resonance circuit to provide vibratory output. In a further embodiment, the circuitry, with the assistance of the appropriate types of deployed electrodes or sensors, is capable of monitoring other types of physiology, in addition to ECGs. Still other types of monitor recorder components and functionality are possible.

The non-conductive receptacle 25 is provided on the top surface of the flexible backing 20 with a retention catch 26 and tension clip 27 molded into the non-conductive receptacle 25 to conformably receive and securely hold the monitor recorder 14 in place. The edges of the bottom surface of the non-conductive receptacle 25 are preferably rounded, and the monitor recorder 14 is nestled inside the interior of the non-conductive receptacle 25 to present a rounded (gentle) surface, rather than a sharp edge at the skin-to-device interface.

The electrode patch 15 is intended to be disposable. The monitor recorder 14, however, is reusable and can be transferred to successive electrode patches 15 to ensure continuity of monitoring. The placement of the wearable monitor 12 in a location at the sternal midline 16 (or immediately to either side of the sternum 13) benefits long-term extended wear by removing the requirement that ECG electrodes be continually placed in the same spots on the skin throughout the monitoring period. Instead, the patient is free to place an electrode patch 15 anywhere within the general region of the sternum 13.

As a result, at any point during ECG monitoring, the patient's skin is able to recover from the wearing of an electrode patch 15, which increases patient comfort and satisfaction, while the monitor recorder 14 ensures ECG monitoring continuity with minimal effort. A monitor recorder 14 is merely unsnapped from a worn out electrode patch 15, the worn out electrode patch 15 is removed from the skin, a new electrode patch 15 is adhered to the skin, possibly in a new spot immediately adjacent to the earlier location, and the same monitor recorder 14 is snapped into the new electrode patch 15 to reinitiate and continue the ECG monitoring.

Figure 4:
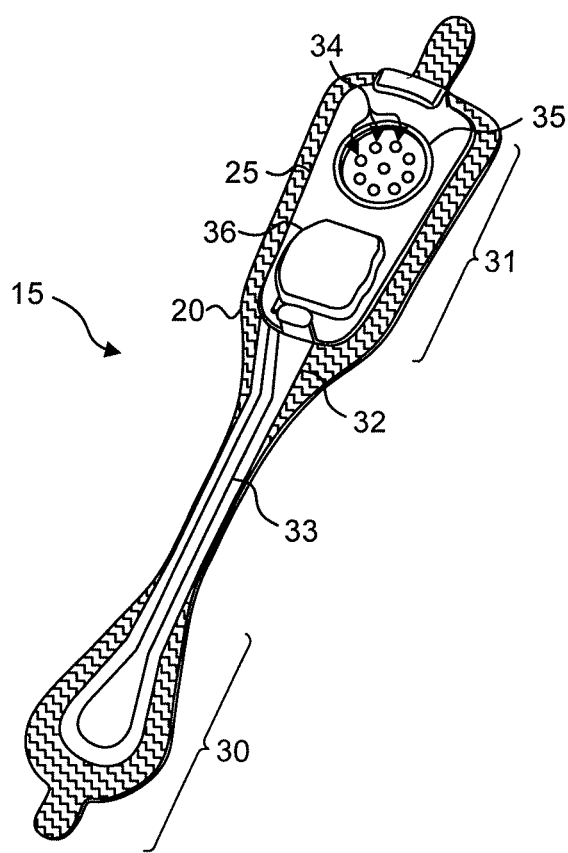
FIG. 4 is a perspective view showing the extended wear electrode patch of FIG. 3 without a monitor recorder inserted.

During use, the electrode patch 15 is first adhered to the skin in the sternal region. FIG. 4 is a perspective view showing the extended wear electrode patch 15 of FIG. 3 without a monitor recorder 14 inserted. A flexible circuit 32 is adhered to each end of the flexible backing 20. A distal circuit trace 33 from the distal end 30 of the flexible backing 20 and a proximal circuit trace (not shown) from the proximal end 31 of the flexible backing 20 electrically couple ECG electrodes (not shown) to a pair of electrical pads 34. The electrical pads 34 are provided within a moisture-resistant seal 35 formed on the bottom surface of the non-conductive receptacle 25. When the monitor recorder 14 is securely received into the non-conductive receptacle 25, that is, snapped into place, the electrical pads 34 interface to electrical contacts (not shown) protruding from the bottom surface of the monitor recorder 14, and the moisture-resistant seal 35 enables the monitor recorder 14 to be worn at all times, even during bathing or other activities that could expose the monitor recorder 14 to moisture.

In addition, a battery compartment 36 is formed on the bottom surface of the non-conductive receptacle 25, and a pair of battery leads (not shown) electrically interface the battery to another pair of the electrical pads 34. The battery contained within the battery compartment 35 can be replaceable, rechargeable or disposable.

The monitor recorder 14 draws power externally from the battery provided in the non-conductive receptacle 25, thereby uniquely obviating the need for the monitor recorder 14 to carry a dedicated power source. The battery contained within the battery compartment 35 can be replaceable, rechargeable or disposable. In a further embodiment, the ECG sensing circuitry of the monitor recorder 14 can be supplemented with additional sensors, including an $SpO_2$ sensor, a blood pressure sensor, a temperature sensor, respiratory rate sensor, a glucose sensor, an air flow sensor, and a volumetric pressure sensor, which can be incorporated directly into the monitor recorder 14 or onto the non-conductive receptacle 25.

The placement of the flexible backing 20 on the sternal midline 16 (or immediately to either side of the sternum 13) also helps to minimize the side-to-side movement of the wearable monitor 12 in the left- and right-handed directions during wear. However, the wearable monitor 12 is still susceptible to pushing, pulling, and torqueing movements, including compressional and torsional forces when the patient bends forward, and tensile and torsional forces when the patient leans backwards. To counter the dislodgment of the flexible backing 20 due to compressional and torsional forces, a layer of non-irritating adhesive, such as hydrocolloid, is provided at least partially on the underside, or contact, surface of the flexible backing 20, but only on the distal end 30 and the proximal end 31. As a result, the underside, or contact surface of the longitudinal midsection 23 does not have an adhesive layer and remains free to move relative to the skin. Thus, the longitudinal midsection 23 forms a crimp relief that respectively facilitates compression and twisting of the flexible backing 20 in response to compressional and torsional forces. Other forms of flexible backing crimp reliefs are possible.

Figure 5:
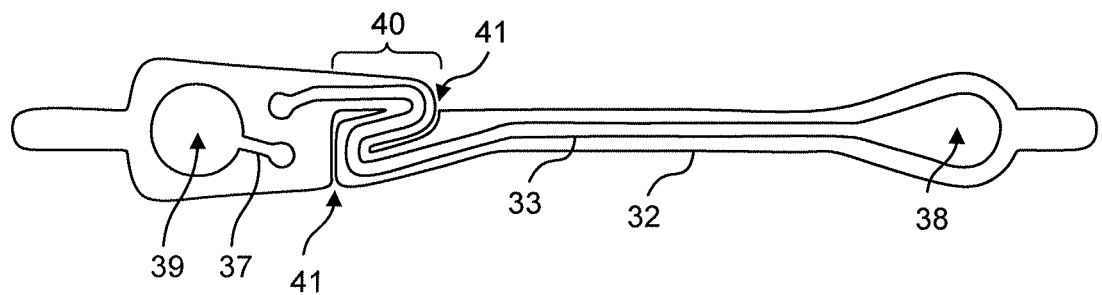
FIG. 5 is a top view showing the flexible circuit of the extended wear electrode patch of FIG. 3.

Unlike the flexible backing 20, the flexible circuit 32 is only able to bend and cannot stretch in a planar direction. FIG. 5 is a top view showing the flexible circuit 32 of the extended wear electrode patch 15 of FIG. 3. A distal ECG electrode 38 and proximal ECG electrode 39 are respectively coupled to the distal and proximal ends of the flexible circuit 32. The flexible circuit 32 preferably does not extend to the outside edges of the flexible backing 20, thereby avoiding gouging or discomforting the patient's skin during extended wear, such as when sleeping on the side. During wear, the ECG electrodes 38, 39 must remain in continual contact with the skin. A strain relief 40 is defined in the flexible circuit 32 at a location that is partially underneath the battery compartment 36 when the flexible circuit 32 is affixed to the flexible backing 20. The strain relief 40 is laterally extendable to counter dislodgment of the ECG electrodes 38, 39 due to tensile and torsional forces. A pair of strain relief cutouts 41 partially extend transversely from each opposite side of the flexible circuit 32 and continue longitudinally towards each other to define in 'S'-shaped pattern, when viewed from above. The strain relief respectively facilitates longitudinal extension and twisting of the flexible circuit 32 in response to tensile and torsional forces. Other forms of circuit board strain relief are possible.

Figure 6:
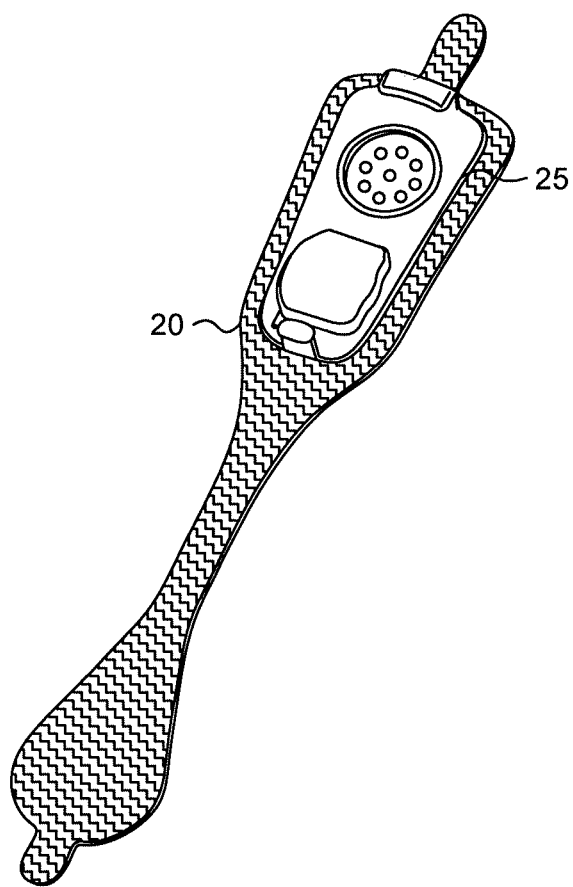
FIG. 6 is a perspective view showing the extended wear electrode patch in accordance with a further embodiment.

The flexible circuit 32 can be provided either above or below the flexible backing 20. FIG. 6 is a perspective view showing the extended wear electrode patch 15 in accordance with a further embodiment. The flexible circuit (not shown) is provided on the underside, or contact, surface of the flexible backing 20 and is electrically interfaced to the set of electrical pads 34 on the bottom surface of the non-conductive receptacle 25 through electrical contacts (not shown) pierced through the flexible backing 20.

Figure 7:
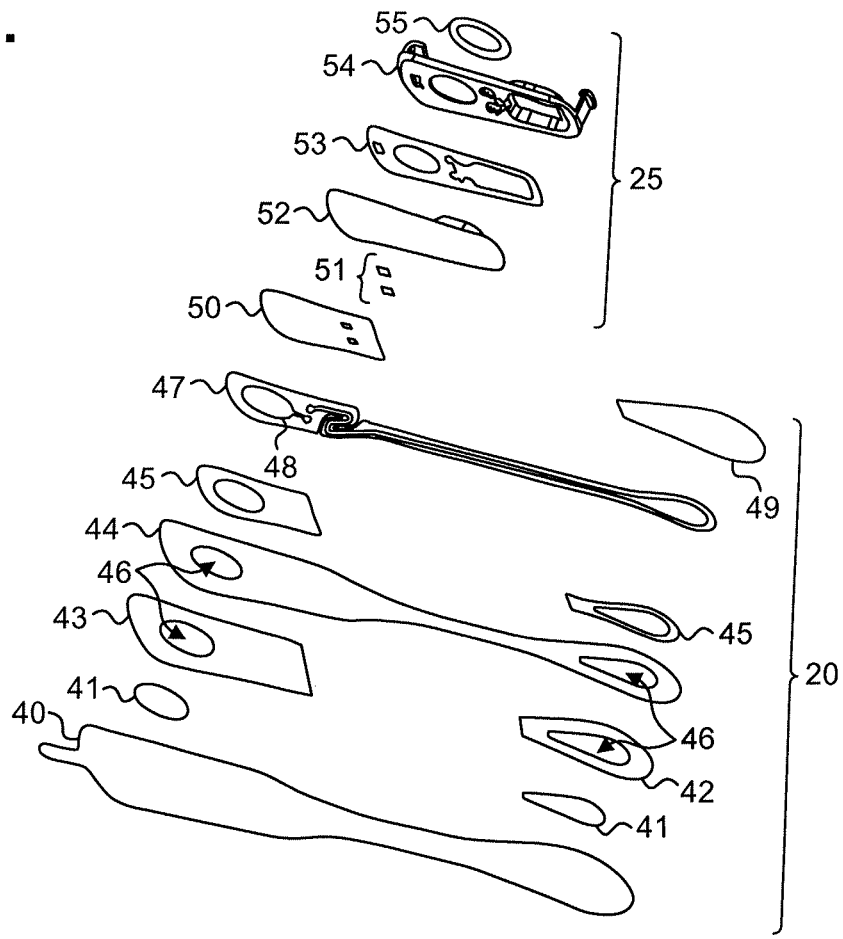
FIG. 7 is an exploded view showing the component layers of the electrode patch of FIG. 3.

The electrode patch 15 is intended to be a disposable component, which enables a patient to replace the electrode patch 15 as needed throughout the monitoring period, while maintaining continuity of physiological sensing through reuse of the same monitor recorder 14. FIG. 7 is an exploded view showing the component layers of the electrode patch 15 of FIG. 3. The flexible backing 20 is constructed of a wearable gauze, latex, or similar wrap knit or stretchable and wear-safe material 44, such as a Tricot-type linen with a pressure sensitive adhesive (PSA) on the underside, or contact, surface. The wearable material 44 is coated with a layer 43 of non-irritating adhesive, such as hydrocolloid, to facilitate long-term wear. The hydrocolloid, for instance, is typically made of mineral oil, cellulose and water and lacks any chemical solvents, so should cause little itching or irritation. Moreover, hydrocolloid is thicker and more gel-like than most forms of PSA and provides cushioning between the relatively rigid and unyielding non-conductive receptacle 25 and the patient's skin. In a further embodiment, the layer of non-irritating adhesive can be contoured, such as by forming the adhesive with a concave or convex cross-section; surfaced, such as through stripes or cross-hatches of adhesive, or by forming dimples in the adhesive's surface; or applied discontinuously, such as with a formation of discrete dots of adhesive.

As described supra with reference to FIG. 5, a flexible circuit can be adhered to either the outward facing surface or the underside, or contact, surface of the flexible backing 20. For convenience, a flexible circuit 47 is shown relative to the outward facing surface of the wearable material 44 and is adhered respectively on a distal end by a distal electrode seal 45 and on a proximal end by a proximal electrode seal 45. In a further embodiment, the flexible circuit 47 can be provided on the underside, or contact, surface of the wearable material 44. Through the electrode seals, only the distal and proximal ends of the flexible circuit 47 are attached to the wearable material 44, which enables the strain relief 40 (shown in FIG. 5) to respectively longitudinally extend and twist in response to tensile and torsional forces during wear. Similarly, the layer 43 of non-irritating adhesive is provided on the underside, or contact, surface of the wearable material 44 only on the proximal and distal ends, which enables the longitudinal midsection 23 (shown in FIG. 3) to respectively bow outward and away from the sternum 13 or twist in response to compressional and torsional forces during wear.

Figure 8:
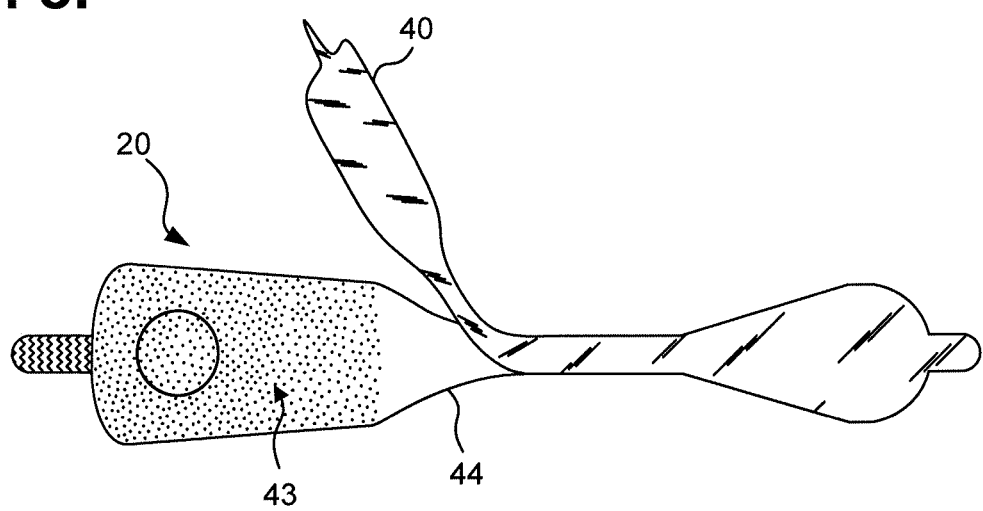
FIG. 8 is a bottom plan view of the extended wear electrode patch of FIG. 3 with liner partially peeled back.

A pair of openings 46 is defined on the distal and proximal ends of the wearable material 44 and layer 43 of non-irritating adhesive for ECG electrodes 38, 39 (shown in FIG. 5). The openings 46 serve as "gel" wells with a layer of hydrogel 41 being used to fill the bottom of each opening 46 as a conductive material that aids electrode signal pick up. The entire underside, or contact, surface of the flexible backing 20 is protected prior to use by a liner layer 40 that is peeled away, as shown in FIG. 8.

The non-conductive receptacle 25 includes a main body 54 that is molded out of polycarbonate, ABS, or an alloy of those two materials to provide a high surface energy to facilitate adhesion of an adhesive seal 53. The main body 54 is attached to a battery printed circuit board 52 by the adhesive seal 53 and, in turn, the battery printed circuit board 52 is adhesed to the flexible circuit 47 with an upper flexible circuit seal 50. A pair of conductive transfer adhesive points 51 or, alternatively, metallic rivets or similar conductive and structurally unifying components, connect the circuit traces 33, 37 (shown in FIG. 5) of the flexible circuit 47 to the battery printed circuit board 52. The main body 54 has a retention catch 26 and tension clip 27 (shown in FIG. 3) that fixably and securely receive a monitor recorder 14 (not shown), and includes a recess within which to circumferentially receive a die cut gasket 55, either rubber, urethane foam, or similar suitable material, to provide a moisture resistant seal to the set of pads 34.

Figure 9:
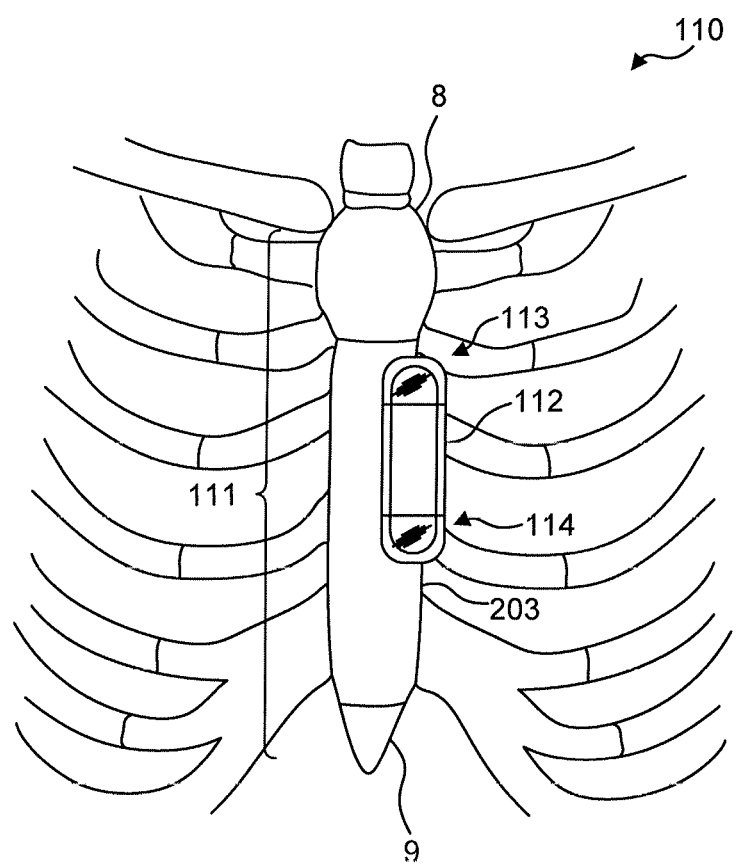
FIG. 9 is a diagram showing, by way of example, a subcutaneous P-wave centric insertable cardiac monitor (ICM) for long term electrocardiographic monitoring in accordance with one embodiment.

In a further embodiment, the P-wave-centric positioning of the cardiac monitor at or near the sternal midline, such as in the parasternal region, with electrodes of the monitor being located at or near the sternum described above, can be adapted for use in a subcutaneous electrocardiography monitor. Long-term electrocardiographic and physiological monitoring over a period lasting up to several years in duration can be provided through a continuously-recording subcutaneous insertable cardiac monitor (ICM), such as one described in commonly-owned U.S. patent application Ser. No. 15/832,385, filed Dec. 5, 2017, pending, the disclosure of which is incorporated by reference. FIG. 9 is a diagram showing, by way of example, a subcutaneous P-wave centric ICM 112 for long term electrocardiographic monitoring in accordance with one embodiment. The ICM 112 is implanted in the parasternal region 111 of a patient 110. The sensing circuitry and components, compression algorithms, and the physical layout of the electrodes are specifically optimized to capture electrical signals from the propagation of low amplitude, relatively low frequency content cardiac action potentials, particularly the P-waves generated during atrial activation. The position and placement of the ICM 112 coupled to engineering considerations that optimize the ICM's sensing circuitry, discussed infra, aid in demonstrating the P-wave clearly.

Implantation of a P-wave centric ICM 112 in the proper subcutaneous site facilitates the recording of high quality ECG data with a good delineation of the P-wave. In general, the ICM 112 is intended to be implanted anteriorly and be positioned axially and slightly to either the right or left of the sternal midline in the parasternal region 111 of the chest, or if sufficient subcutaneous fat exists, directly over the sternum. Optimally, the ICM 112 is implanted in a location left parasternally to bridge the left atrial appendage. However, either location to the right or left of the sternal midline is acceptable; placement of the device, if possible, should bridge the vertical height of the heart, which lies underneath the sternum 103, thereby placing the ICM 112 in close proximity to the anterior right atrium and the left atrial appendage that lie immediately beneath.

The ICM 112 is shaped to fit comfortably within the body under the skin and to conform to the contours of the patient's parasternal region 111 when implanted immediately to either side of the sternum 103, but could be implanted in other locations of the body. In most adults, the proximal end 113 of the ICM 112 is generally positioned below the manubrium 8 but, depending upon patient's vertical build, the ICM 112 may actually straddle the region over the manubrium 8. The distal end 114 of the ICM 112 generally extends towards the xiphoid process 9 and lower sternum but, depending upon the patient's build, may actually straddle the region over or under the xiphoid process 9, lower sternum and upper abdomen.

Although internal tissues, body structures, and tissue boundaries can adversely affect the current strength and signal fidelity of all body surface potentials, subsurface low amplitude cardiac action potentials, particularly P-wave signals with a normative amplitude of less than 0.25 millivolts (mV) and a normative duration of less than 120 milliseconds (ms), are most apt to be negatively impacted by these factors. The atria, which generate the P wave, are mostly located posteriorly within the thoracic cavity (with the exception of the anterior right atrium, right atrial appendage and left atrial appendage). The majority of the left atrium constitutes the portion of the heart furthest away from the surface of the skin on the chest and harbors the atrial tissue most likely to be the source of serious arrhythmias, like atrial fibrillation. Conversely, the ventricles, which generate larger amplitude signals, are located anteriorly as in the case of the anterior right ventricle and most of the anterior left ventricle situated relatively close to the skin surface of the central and left anterior chest. These factors, together with larger size and more powerful impulse generation from the ventricles, contribute to the relatively larger amplitudes of ventricular waveforms.

Nevertheless, as explained supra, both the P-wave and the R-wave are required for the physician to make a proper rhythm diagnosis from the dozens of arrhythmias that can occur. Yet, the quality of P-waves is more susceptible to weakening from distance and the intervening tissues and structures and from signal attenuation and signal processing than the high voltage waveforms associated with ventricular activation. The added value of avoiding further signal attenuation resulting from dermal impedance makes a subcutaneous P-wave centric ICM even more likely to match, or even outperform dermal ambulatory monitors designed to analogous engineering considerations and using similar sensing circuitry and components, compression algorithms, and physical layout of electrodes, such as described in U.S. Pat. No. 9,545,204, issued Jan. 17, 2017 to Bishay et al.; U.S. Pat. No. 9,730,593, issued Aug. 15, 2017 to Felix et al.; U.S. Pat. No. 9,700,227, issued Jul. 11, 2017 to Bishay et al.; U.S. Pat. No. 9,717,433, issued Aug. 1, 2017 to Felix et al.; and U.S. Pat. No. 9,615,763, issued Apr. 11, 2017 to Felix et al., the disclosures of which are incorporated by reference.

The ICM 112 can be implanted in the patient's chest using, for instance, a minimally invasive subcutaneous implantation instrument or other suitable surgical implement. The ICM 112 is positioned slightly to the right or left of midline, covering the center third of the chest, roughly between the second and sixth ribs, approximately spanning between the level of the manubrium 8 and the level of the xiphoid process 9 on the inferior border of the sternum 103, depending upon the vertical build of the patient 110.

During monitoring, the amplitude and strength of action potentials sensed by an ECG devices, including dermal ECG monitors and ICMs, can be affected to varying degrees by cardiac, cellular, extracellular, vector of current flow, and physical factors, like obesity, dermatitis, lung disease, large breasts, and high impedance skin, as can occur in dark-skinned individuals. Performing ECG sensing subcutaneously in the parasternal region 111 significantly improves the ability of the ICM 112 to counter some of the effects of these factors, particularly high skin impedance and impedance from subcutaneous fat. Thus, the ICM 112 exhibits superior performance when compared to conventional dermal ECG monitors to existing implantable loop recorders, ICMs, and other forms of implantable monitoring devices by virtue of its engineering and proven P-wave documentation above the skin, as discussed in W. M. Smith et al., "Comparison of diagnostic value using a small, single channel, P-wave centric sternal ECG monitoring patch with a standard 3-lead Holter system over 24 hours," Am. Heart J., March 2017; 185:67-73, the disclosure of which is incorporated by reference.

Moreover, the sternal midline implantation location in the parasternal region 111 allows the ICM's electrodes to record an ECG of optimal signal quality from a location immediately above the strongest signal-generating aspects of the atrial. Signal quality is improved further in part because cardiac action potential propagation travels simultaneously along a north-to-south and right-to-left vector, beginning high in the right atrium and ultimately ending in the posterior and lateral region of the left ventricle. Cardiac depolarization originates high in the right atrium in the SA node before concurrently spreading leftward towards the left atrium and inferiorly towards the atrioventricular (AV) node. On the proximal end 113, the ECG electrodes of the ICM 112 are subcutaneously positioned with the upper or superior pole (ECG electrode) slightly to the right or left of the sternal midline in the region of the manubrium 8 and, on the distal end 114, the lower or inferior pole (ECG electrode) is similarly situated slightly to the right or left of the sternal midline in the region of the xiphoid process 9 and lower sternum 103. The ECG electrodes of the ICM 112 are placed primarily in a north-to-south orientation along the sternum 103 that corresponds to the north-to-south waveform vector exhibited during atrial activation. This orientation corresponds to the aVF lead used in a conventional 12-lead ECG that is used to sense positive or upright P-waves. In addition, the electrode spacing and the electrodes' shapes and surface areas mimic the electrodes used in the ICM's dermal cousin, designed as part of the optimal P-wave sensing electrode configuration, such as provided with the dermal ambulatory monitors cited supra.

Figure 10:
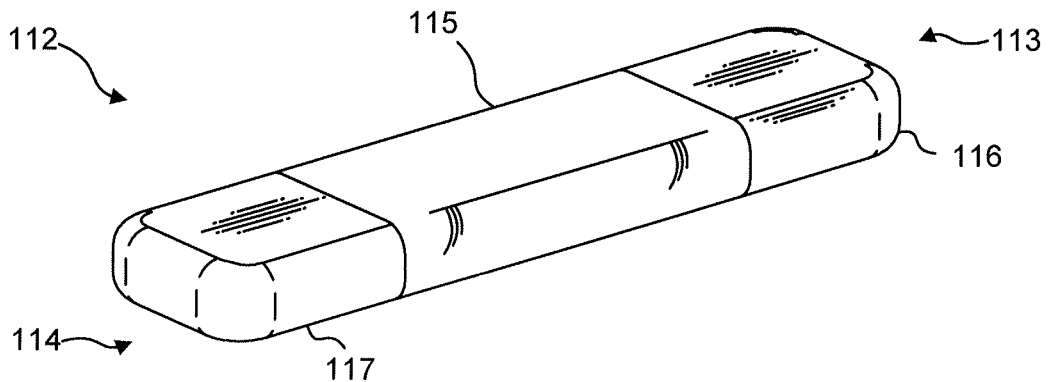
FIGS. 10 and 11 are respectively top and bottom perspective views showing the ICM of FIG. 9.
Figure 11:
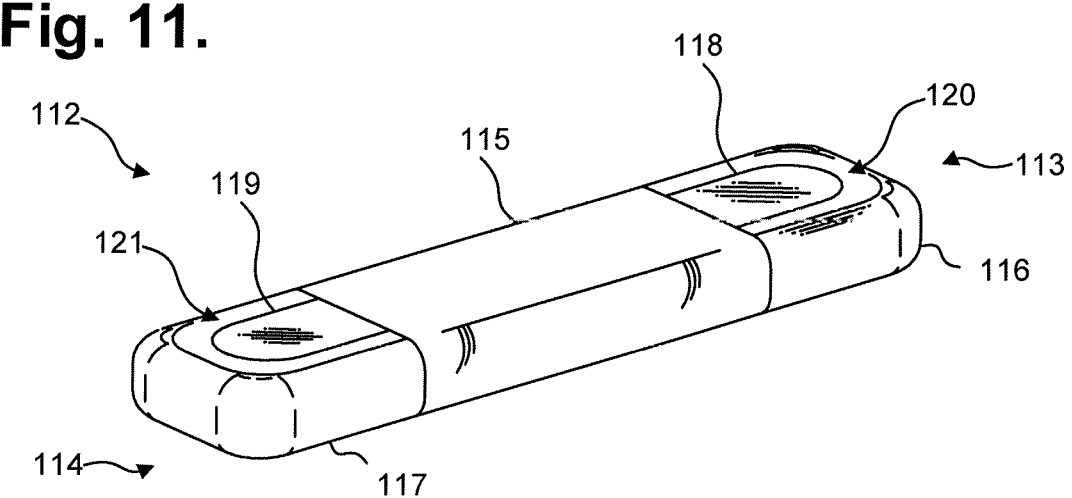

Despite the challenges faced in capturing low amplitude cardiac action potentials, the ICM 112 is able to operate effectively using only two electrodes that are strategically sized and placed in locations ideally suited to high fidelity P-wave signal acquisition. This approach has been shown to clinically outperform more typical multi-lead monitors because of the improved P-wave clarity, as discussed in W. M. Smith et al., cited supra. FIGS. 10 and 11 are respectively top and bottom perspective views showing the ICM 112 of FIG. 9. Physically, the ICM 112 is constructed with a hermetically sealed implantable housing 115 with at least one ECG electrode forming a superior pole on the proximal end 113 and at least one ECG electrode forming an inferior pole on the distal end 114.

When implanted, the housing 115 is oriented most cephalad. The housing 115 is constructed of titanium, stainless steel or other biocompatible material. The housing 115 contains the sensing, recordation and interfacing circuitry of the ICM 112, plus a long life battery. A wireless antenna is integrated into or within the housing 115 and can be positioned to wrap around the housing's internal periphery or location suited to signal reception. Other wireless antenna placement or integrations are possible.

Physically, the ICM 112 has four ECG electrodes 116, 117, 118, 119. There could also be additional ECG electrodes, as discussed infra. The ECG electrodes include two ventral (or dorsal) ECG electrodes 118, 119 and two wraparound ECG electrodes 116, 117. One ventral ECG electrode 118 is formed on the proximal end 113 and one ventral ECG electrode 119 is formed on the distal end 114. One wraparound ECG electrode 116 is formed circumferentially about the proximal end 113 and one wraparound ECG electrode 117 is formed circumferentially about the distal end 114. Each wraparound ECG electrode 116, 117 is electrically insulated from its respective ventral ECG electrode 118, 119 by a periphery 120, 121.

The four ECG electrodes 116, 117, 118, 119 are programmatically controlled by a microcontroller through onboard firmware programming to enable a physician to choose from several different electrode configurations that vary the electrode surface areas, shapes, and inter-electrode spacing. The sensing circuitry can be programmed, either pre-implant or in situ, to use different combinations of the available ECG electrodes (and thereby changing electrode surface areas, shapes, and inter-electrode spacing), including pairing the two ventral ECG electrodes 116, 117, the two wraparound ECG electrodes 118, 119, or one ventral ECG electrode 116, 117 with one wraparound ECG electrode 118, 119 located on the opposite end of the housing 115. In addition, the periphery 120, 121 can be programmatically controlled to logically combine the wraparound ECG electrode 116, 117 on one end of the ICM 112 with its corresponding ventral ECG electrode 118, 119 to form a single virtual ECG electrode with larger surface area and shape. (Although electronically possible, the two ECG electrodes that are only on one end of the ICM 112, for instance, wraparound ECG electrode 116 and ventral ECG electrode 118, could be paired; however, the minimal inter-electrode spacing would likely yield a signal of poor fidelity in most situations.)

In a further embodiment, the housing 115 and contained circuitry can be provided as a standalone ICM core assembly to which a pair of compatible ECG electrodes can be operatively coupled to form a full implantable ICM device.

Figure 12:
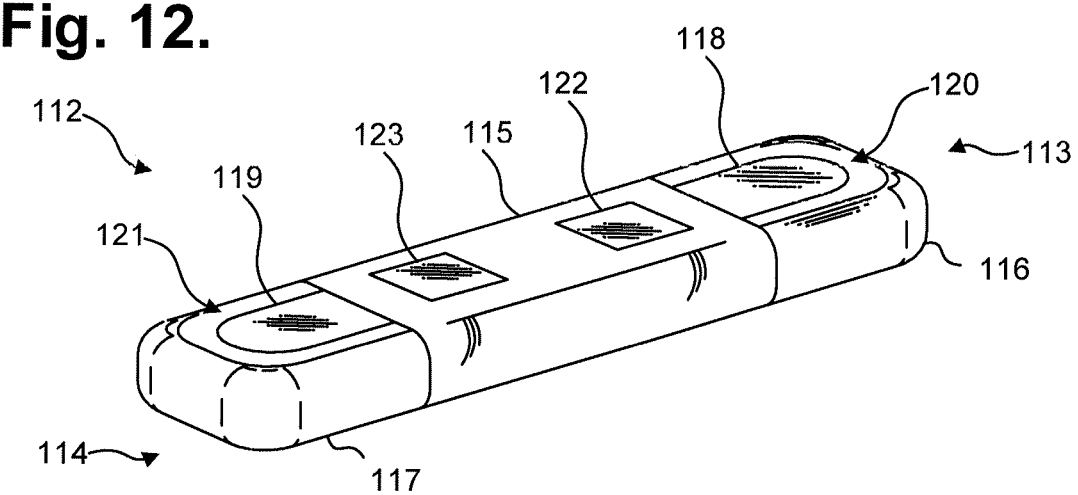
FIG. 12 is a bottom perspective view showing the ICM of FIG. 9 in accordance with a further embodiment.

Other ECG electrode configurations are possible. For instance, additional ECG electrodes can be provided to increase the number of possible electrode configurations, all of which are to ensure better P-wave resolution. FIG. 12 is a bottom perspective view showing the ICM 112 of FIG. 9 in accordance with a further embodiment. An additional pair of ventral ECG electrodes 122, 123 are included on the housing's ventral surface. These ventral ECG electrodes 122, 123 are spaced closer together than the ventral ECG electrodes 118, 119 on the ends of the housing 115 and a physician can thus choose to pair the two inner ventral ECG electrodes 122, 123 by themselves to allow for minimal electrode-to-electrode spacing, or with the other ECG electrodes 116, 117, 118, 119 to vary electrode surface areas, shapes, and inter-electrode spacing even further to explore optimal configurations to acquire the P-wave.

Figure 13:
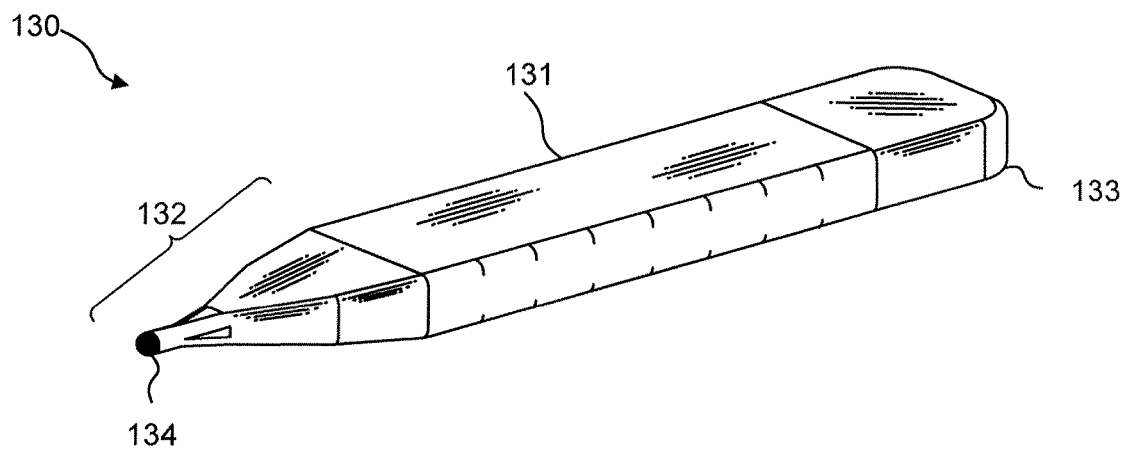
FIGS. 13 and 14 are respectively top and bottom perspective views showing an ICM in accordance with a still further embodiment.
Figure 14:
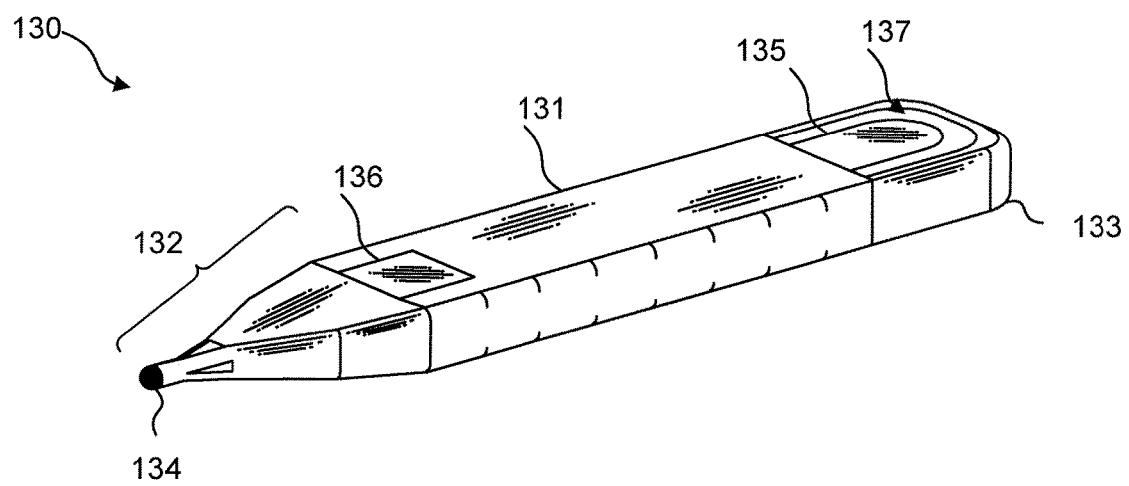

Other housing configurations of the ICM are possible. For instance, the housing of the ICM can be structured to enhance long term comfort and fitment, and to accommodate a larger long life battery or more circuitry or features, including physiologic sensors, to provide additional functionality. FIGS. 13 and 14 are respectively top and bottom perspective views showing an ICM 130 in accordance with a still further embodiment. The ICM 230 has a housing 131 with a tapered extension 132 that is terminated on the distal end with an electrode 134. On a proximal end, the housing 131 includes a pair of ECG electrodes electrically insulated by a periphery 137 that include a ventral ECG electrode 133 and a wraparound ECG electrode 134. In addition, a ventral ECG electrode 136 is oriented on the housing's distal end before the tapered extension 132. Still other housing structures and electrode configurations are possible.

In general, the basic electrode layout is sufficient to sense cardiac action potentials in a wide range of patients. Differences in thoracic tissue density and skeletal structure from patient to patient, though, can affect the ability of the sensing electrodes to efficaciously capture action potential signals, yet the degree to which signal acquisition is affected may not be apparent until after an ICM has been implanted and deployed, when the impacts of the patient's physical constitution and his patterns of mobility and physical movement on ICM monitoring can be fully assessed.

Figure 15:
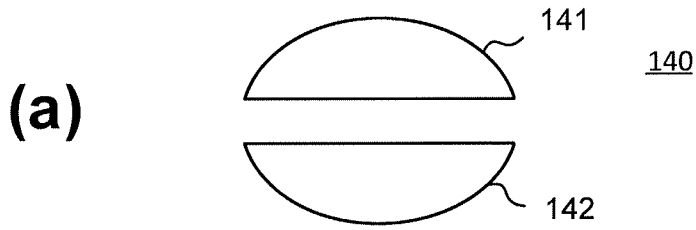
FIG. 15 is a plan view showing further electrode configurations.
Figure 15:
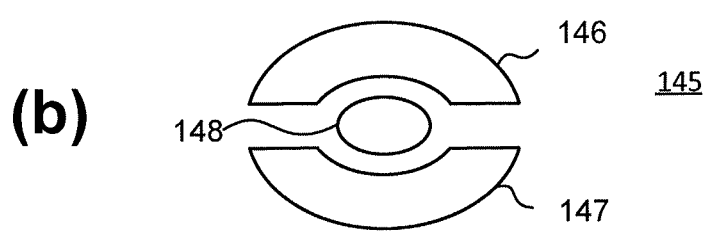

In further embodiments, the electrodes can be configured post-implant to allow the ICM to better adapt to a particular patient's physiology. For instance, electrode configurations having more than two sensing electrodes are possible. FIG. 15 is a plan view showing further electrode configurations. Referring first to FIG. 15(a), a single disc ECG electrode 140 could be bifurcated to form a pair of half-circle ECG electrodes 141, 142 that could be programmatically selected or combined to accommodate a particular patients ECG signal characteristics post-ICM implant. Referring next to FIG. 15(b), a single disc ECG electrode 145 could be divided into three sections, a pair of crescent-shaped ECG electrodes 146, 147 surrounding a central semicircular ECG electrode 148 that could similarly be programmatically selected or combined. Still other ECG electrode configurations are possible.

While the invention has been particularly shown and described as referenced to the embodiments thereof, those skilled in the art will understand that the foregoing and other changes in form and detail may be made therein without departing from the spirit and scope.

What is claimed is:

1. A subcutaneous insertable electrocardiography (ECG) monitor, comprising:
   an implantable housing comprised of a biocompatible material that is suitable for implantation within a living body in at least one of the sternal midline and the parasternal region of the chest of the body;
   at least a pair of ECG sensing electrodes provided on a ventral surface and on opposite ends of the implantable housing operatively placed to facilitate sensing in closest proximity to the low amplitude, low frequency content cardiac action potentials that are generated during atrial activation, one of the electrodes being disposed for being positioned in at least one a region overlying the inferior sternum and the parasternal region of a patient's chest when the housing has been implanted, the other of the electrodes being disposed for being positioned in at least one of the superior sternal region and the parasternal region of the patient's chest when the housing has been implanted;
   an extension formed on a distal end of the implantable housing;
   at least one additional ECG sensing electrode provided on a distal end of the extension, the at least one additional ECG sensing electrode comprising a pair of crescent-shaped electrodes surrounding a central oval electrode that can be programmatically combined by the microcontroller to form a single electrode; and
   electronic circuitry provided within the housing assembly comprising the low power microcontroller operable to execute under modular micro program control as specified in firmware, an ECG front end circuit interfaced to the microcontroller and configured to capture the cardiac action potentials sensed by the pair of ECG sensing electrodes which are output as ECG signals, and non-volatile memory electrically interfaced with the microcontroller and operable to continuously store samples of the ECG signals, wherein the firmware comprises programmatic selection of one or more pairings of the ECG sensing electrodes.

2. A monitor in accordance with claim 1, wherein the implantable housing is configured to be positioned between the second and the sixth rib of the body.

3. A monitor in accordance with claim 1, wherein the biocompatible material comprises at least one of titanium and stainless steel.

4. A monitor in accordance with claim 1, further comprising:
   a wireless antenna positioned to wrap around an internal periphery of the implantable housing.

5. A monitor in accordance with claim 1, further comprising:
   at least one further ECG sensing electrode further provided to wraparound an end of the implantable housing circumferentially about one of the pair of ECG sensing electrodes, continue around the sides and ends of the implantable housing, and over the planar surface of the implantable housing.

6. A monitor in accordance with claim 5, wherein one of the ECG sensing electrodes and the at least one ECG sensing electrode are logically combined to form a single virtual electrode.

7. A monitor in accordance with claim 5, wherein the at least one further ECG sensing electrode is electrically insulated from at least one of the ECG sensing electrodes.

8. A monitor in accordance with claim 1, wherein the pair of the ECG sensing electrodes are operatively coupled to the implantable housing.

9. A rectangular subcutaneous insertable electrocardiography monitor, comprising:
   a hermetically sealed implantable housing defining a rectangular shape with rounded edges and comprised of a biocompatible material that is suitable for implantation within a living body of a patient in at least one of the sternal midline and the parasternal region of the chest of the body;
   at least a pair of ECG sensing electrodes provided on a ventral surface and on opposite ends of the implantable housing operatively placed to facilitate sensing in closest proximity to the low amplitude, low frequency content cardiac action potentials that are generated during atrial activation, one of the electrodes being disposed for being positioned in at least one a region overlying the inferior sternum and the parasternal region of a patient's chest when the housing has been implanted, the other of the electrodes being disposed for being positioned in at least one of the superior sternal region and the parasternal region of the patient's chest when the housing has been implanted;
   an extension formed on a distal end of the implantable housing and tapering from a proximal end of the extension and towards a distal end of the extension, the distal end of the tapered extension comprising a substantially cylindrical structure;
   at least one additional ECG sensing electrode provided on a distal end of the cylindrical structure, the at least one additional ECG sensing electrode comprising a pair of crescent-shaped electrodes surrounding a central oval electrode that can be programmatically combined by a low-power microcontroller to form a single electrode; and
   electronic circuitry provided within the housing assembly comprising the low power microcontroller operable to execute under modular micro program control as specified in firmware, an ECG front end circuit interfaced to the microcontroller and configured to capture the cardiac action potentials sensed by the pair of ECG sensing electrodes which are output as ECG signals, and non-volatile memory electrically interfaced with the microcontroller and operable to continuously store samples of the ECG signals, wherein the firmware comprises programmatic selection of one or more pairings of the ECG sensing electrodes.

10. A monitor in accordance with claim 9, wherein the implantable housing is configured to be positioned between the second and the sixth rib of the body.

11. A monitor in accordance with claim 9, wherein the biocompatible material comprises at least one of titanium and stainless steel.

12. A monitor in accordance with claim 9, further comprising:
    a wireless antenna positioned to wrap around an internal periphery of the implantable housing.

13. A monitor in accordance with claim 9, further comprising:
    at least one further ECG sensing electrode further provided to wraparound an end of the implantable housing circumferentially about one of the pair of ECG sensing electrodes, continue around the sides and ends of the implantable housing, and over the planar surface of the implantable housing.

14. A monitor in accordance with claim 13, wherein one of the ECG sensing electrodes and the at least one ECG sensing electrode are logically combined to form a single virtual electrode.

15. A monitor in accordance with claim 13, wherein the at least one further ECG sensing electrode is electrically insulated from at least one of the ECG sensing electrodes.

16. A monitor in accordance with claim 9, wherein the pair of the ECG sensing electrodes are operatively coupled to the implantable housing.

* * * * *